(12) United States Patent
Namii et al.

(10) Patent No.: US 8,345,084 B2
(45) Date of Patent: Jan. 1, 2013

(54) STEREOSCOPIC IMAGE-CAPTURING OBJECTIVE OPTICAL SYSTEM AND ENDOSCOPE

(75) Inventors: Yasushi Namii, Hachioji (JP); Hideyasu Takato, Hino (JP)

(73) Assignee: Olympus Medical Systems Corp., Tokyo (JP)

(*) Notice: Subject to any disclaimer, the term of this patent is extended or adjusted under 35 U.S.C. 154(b) by 8 days.

(21) Appl. No.: 13/135,078

(22) Filed: Jun. 23, 2011

(65) Prior Publication Data

US 2012/0075448 A1 Mar. 29, 2012

Related U.S. Application Data

(63) Continuation of application No. PCT/JP2010/068672, filed on Oct. 22, 2010.

(30) Foreign Application Priority Data

Oct. 23, 2009 (JP) ................................. 2009-244658

(51) Int. Cl.
*A61B 1/05* (2006.01)

(52) U.S. Cl. ............................... 348/45; 348/49; 348/68

(58) Field of Classification Search .................... 348/45, 348/49, 68
See application file for complete search history.

(56) References Cited

U.S. PATENT DOCUMENTS

| 5,743,846 A * | 4/1998 | Takahashi et al. | ............ 600/166 |
| 6,603,876 B1 * | 8/2003 | Matsuo et al. | ................ 382/154 |

FOREIGN PATENT DOCUMENTS

| JP | 7-323012 | 12/1995 |
| JP | 08-056891 | 3/1996 |
| JP | 8-234339 | 9/1996 |
| JP | 11-258516 | 9/1999 |
| JP | 2000-23199 | 1/2000 |
| JP | 2000-81331 | 3/2000 |
| JP | 2003-5096 | 1/2003 |
| JP | 2004-004869 | 1/2004 |

* cited by examiner

Primary Examiner — Sath V Perungavoor
Assistant Examiner — Jeffery Williams
(74) Attorney, Agent, or Firm — Kenyon & Kenyon LLP

(57) ABSTRACT

A system includes a first prism pair that converts beams emitted from a subject and having two substantially parallel optical axes arranged side-by-side in one direction into beams arranged side-by-side in a direction intersecting the aforementioned side-by-side direction; and a second prism pair that performs conversion to reduce the distance between the optical axes of the two beams converted by the first prism pair and that has exit surfaces arranged side-by-side in a direction perpendicular to the side-by-side arrangement direction before entering the first prism pair. The first prism pair includes a first parallelogram prism that reflects, twice, the beam containing one of the two optical axes in a first plane containing one of the optical axes, and a second parallelogram prism that reflects, twice, the beam containing the other of the two optical axes in a second plane containing the other optical axis and parallel to the first plane.

7 Claims, 31 Drawing Sheets

SPHERICAL ABERRATION (XZ)
Fno6.0

SPHERICAL ABERRATION (YZ)

SPHERICAL ABERRATION (XZ)
Fno6.1

SPHERICAL ABERRATION (YZ)

SPHERICAL ABERRATION (XZ)
Fno6.2

SPHERICAL ABERRATION (YZ)

SPHERICAL ABERRATION (XZ)
Fno6.2

SPHERICAL ABERRATION (YZ)

STEREOSCOPIC IMAGE-CAPTURING OBJECTIVE OPTICAL SYSTEM AND ENDOSCOPE

CROSS REFERENCE TO RELATED APPLICATIONS

This is a continuation of International Application PCT/JP/2010/068672, with an international filing date of Oct. 22, 2010, which is hereby incorporated by reference herein in its entirety. This application claims the benefit of Japanese Patent Application No. 2009-244658, the content of which is incorporated herein by reference.

TECHNICAL FIELD

The present invention relates to stereoscopic image-capturing objective optical systems and endoscopes.

BACKGROUND ART

Conventionally known stereoscopic image-capturing optical systems capture two parallax images of a single subject by dividing a single image-capturing surface into two (for example, see PTLs 1 and 2). In PTLs 1 and 2, two parallax images arranged in a direction perpendicular to the direction in which parallax occurs are captured. Thus, a stereoscopic image can be captured without sacrificing the resolution in the direction in which parallax occurs, which is important in stereoscopic image-capturing.

CITATION LIST

Patent Literature

{PTL 1} Japanese Unexamined Patent Application, Publication No. Hei 8-234339
{PTL 2} Japanese Unexamined Patent Application, Publication No. 2004-4869

SUMMARY OF INVENTION

Technical Problem

The present invention provides a stereoscopic image-capturing objective optical system and an endoscope that are reduced in size, suppress tilting of two parallax images with ease, and can capture a bright stereoscopic image.

Solution to Problem

A first aspect of the present invention is a stereoscopic image-capturing objective optical system including a first prism pair that converts beams emitted from a single subject and having two substantially parallel optical axes arranged side-by-side in one direction with a certain distance therebetween into beams arranged side-by-side in a direction intersecting the aforementioned side-by-side direction with a certain distance therebetween; and a second prism pair that performs conversion to reduce the distance between the optical axes of the two beams converted by the first prism pair and that has exit surfaces arranged side-by-side in a direction perpendicular to the side-by-side arrangement direction before entering the first prism pair.

A second aspect of the present invention is an endoscope having the above stereoscopic image-capturing objective optical system at the tip of an insertion portion thereof.

DESCRIPTION OF EMBODIMENTS

A stereoscopic image-capturing objective optical system and an endoscope according to an embodiment of the present invention will be described below with reference to the drawings.

Figure 1:
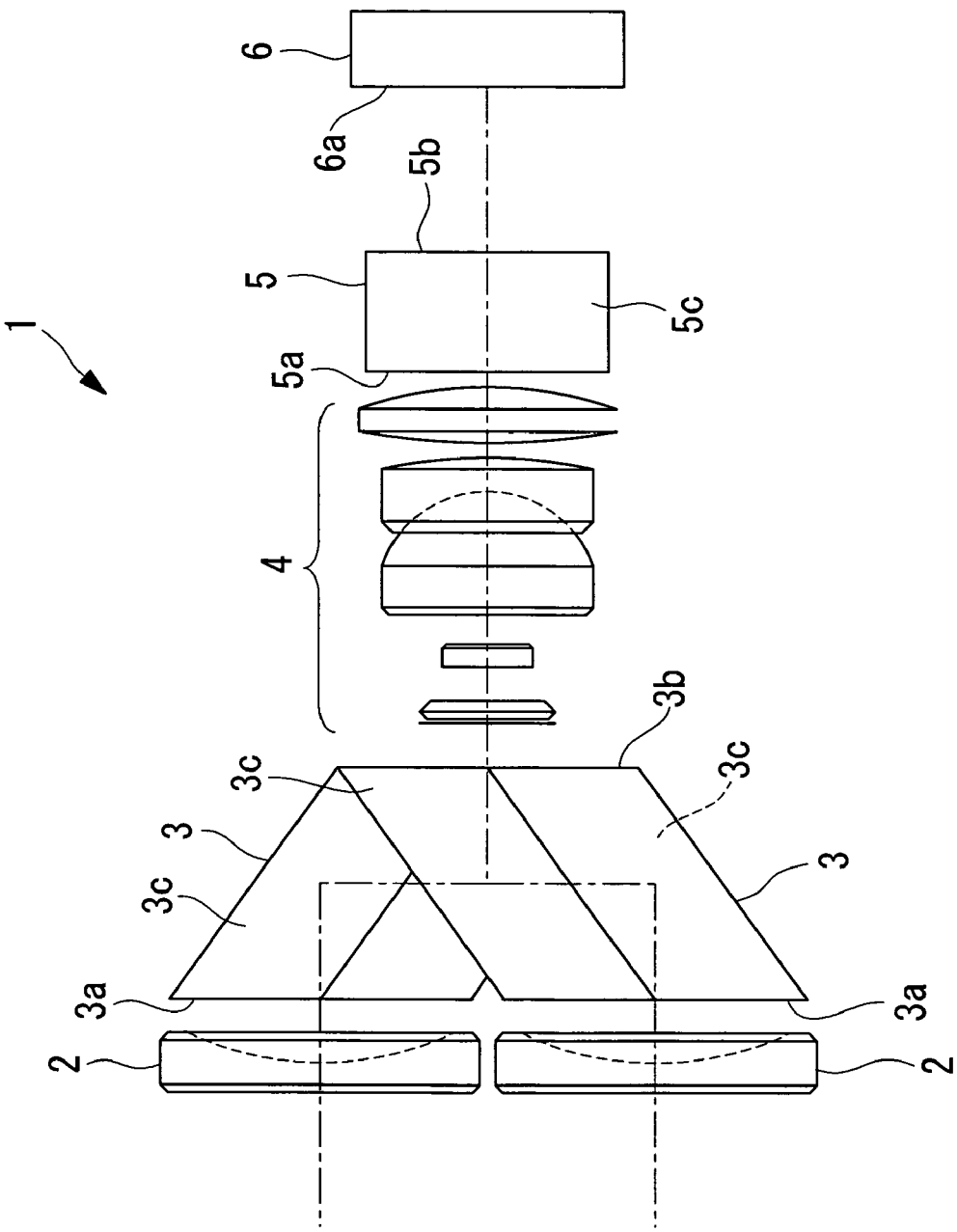
FIG. 1 is an (XZ) plan view showing the overall configuration of a stereoscopic image-capturing objective optical system according to an embodiment of the present invention.
Figure 2:
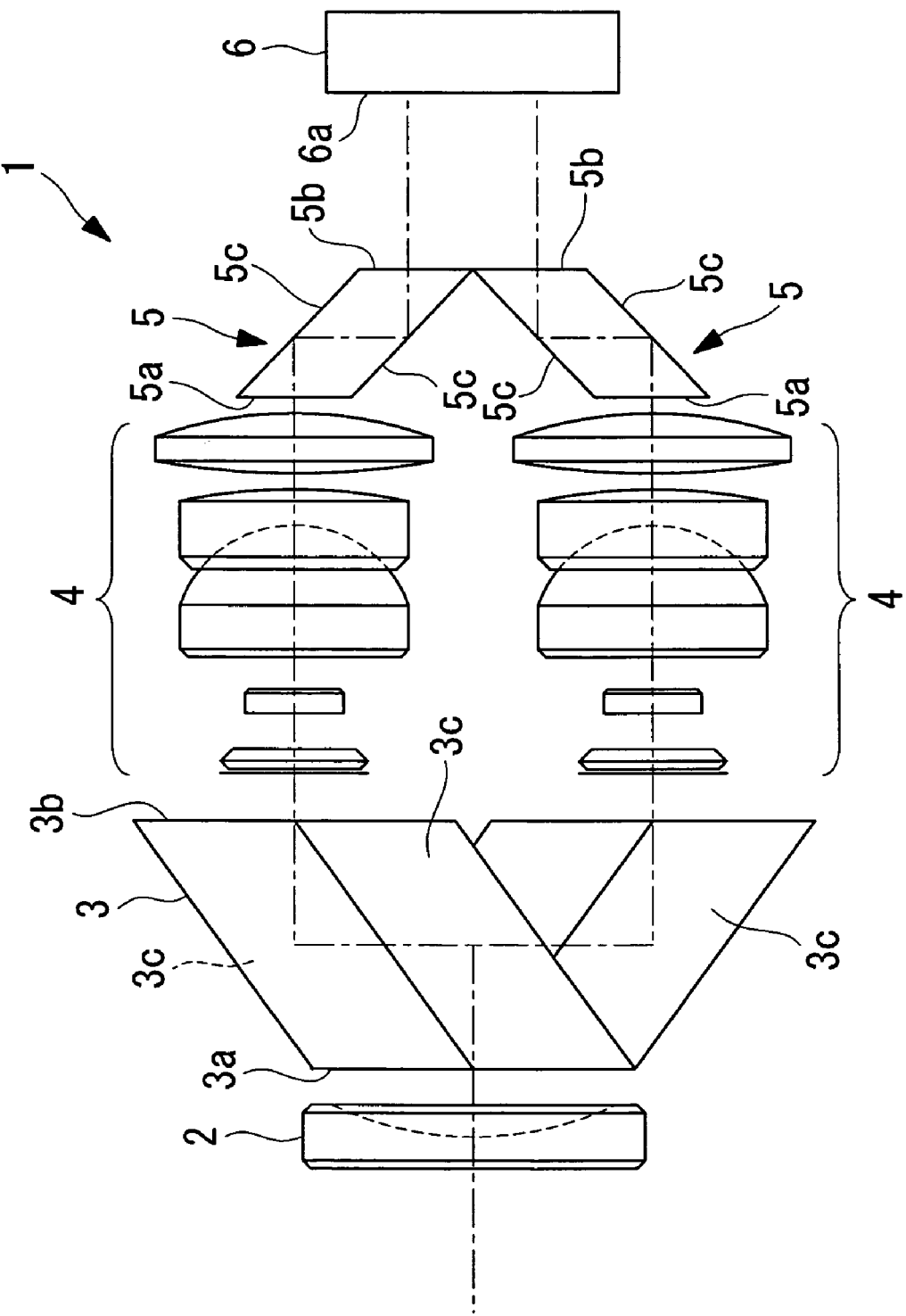
FIG. 2 is a (YZ) side view of the stereoscopic image-capturing objective optical system in FIG. 1.
Figure 3:
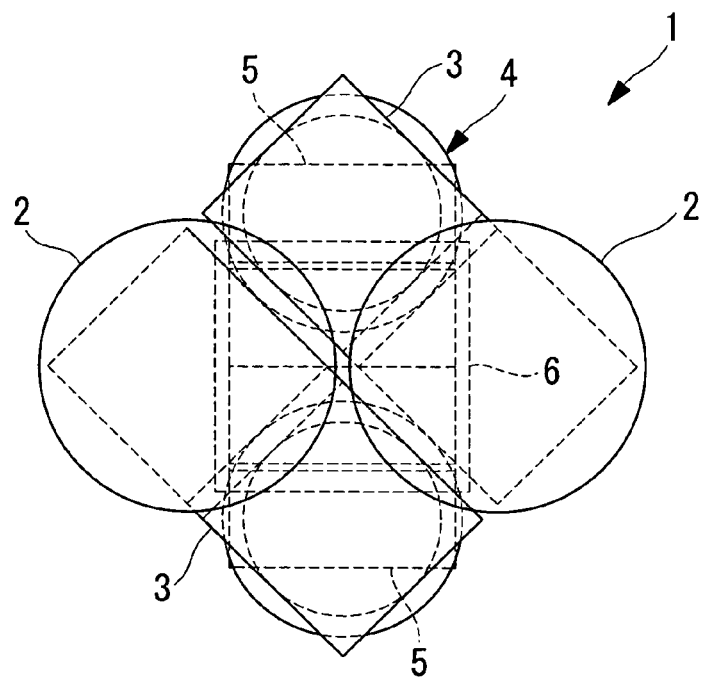
FIG. 3 is a front view of the stereoscopic image-capturing objective optical system in FIG. 1, viewed from an object side.

A stereoscopic image-capturing objective optical system 1 according to this embodiment is disposed at the tip of an insertion portion of an endoscope and, as shown in FIGS. 1 to 3, includes a pair of first lens groups 2 disposed on the object side, a pair of first prisms (a first prism pair) 3 that shift two beams passing through the pair of first lens groups 2, a pair of second lens groups 4 that allow the two beams passing through the pair of first prisms 3 to pass therethrough, and a pair of second prisms (a second prism pair) 5 that shift the two beams passing through the pair of second lens groups 4 such that their optical axes approach each other.

As shown in FIGS. 1 and 3, the first lens groups 2 are arranged side-by-side in one direction and have negative refractive power. Thus, the first lens groups 2 focus light emitted from a large area of a subject disposed on the object side and form two substantially collimated beams. The two beams formed by the pair of first lens groups 2 are substantially parallel to each other with a certain distance therebetween.

The prisms 3 constituting the first prism pair are each a parallelogram prism composed of a six-sided parallelepiped. Each prism 3 includes an entrance surface 3a, an exit surface 3b, which are parallel to each other, and two parallel reflecting surfaces 3c disposed between the entrance surface 3a and the exit surface 3b. When the beams formed by the first lens groups 2 enter the prisms 3 from the entrance surfaces 3a of the prisms 3 constituting the first prism pair, the beams are reflected twice by the two reflecting surfaces 3c in the prisms 3 and exit from the exit surfaces 3b.

As shown in FIGS. 1 to 3, the entrance surfaces 3a of the prisms 3, constituting the first prism pair, are disposed such that their center positions are aligned with the optical axes of the pair of first lens groups 2. Furthermore, the exit surfaces 3b of the prisms 3 are disposed such that their center positions are arranged side-by-side in a direction perpendicular to the direction in which the pair of first lens groups 2 are arranged side-by-side. That is, the pair of first prisms 3 convert the beams so as to rotate the side-by-side direction of the optical axes of the pair of first lens groups 2 by 90°.

Furthermore, the pair of second lens groups 4 have positive refractive power that focuses the beams that exit from the exit surfaces 3b of the prisms 3 of the first prism pair. Furthermore, a plurality of lenses are arranged in each second lens group 4, and one or more of these lenses has a toric surface. A toric surface gives a beam passing therethrough different magnifications in two directions perpendicular to each other. In this embodiment, a smaller magnification is given in the direction perpendicular to the side-by-side direction of the first lens groups 2.

The prisms 5 constituting the second prism pair are also each a parallelogram prism composed of a six-sided parallelepiped. Each prism 5 includes an entrance surface 5a, an exit surface 5b, which are parallel to each other, and two parallel reflecting surfaces 5c disposed between the entrance surface 5a and the exit surface 5b. When the beams formed by the second lens groups 4 enter the prisms 5 from the entrance surfaces 5a of the prisms 5 constituting the second prism pair, the beams are reflected twice by the two reflecting surfaces 5c in the prisms 5 and exit from the exit surfaces 5b.

Furthermore, as shown in FIGS. 1 to 3, the entrance surfaces 5a of the prisms 5, constituting the second prism pair, are disposed such that their center positions are aligned with the optical axes of the pair of second lens groups 4. Furthermore, the exit surfaces 5b of the prisms 5 are disposed so as to reduce the distance between the optical axes of the beams that exit from the pair of second lens groups 4. That is, by passing through the pair of second prisms 5, the two beams passing through the pair of second lens groups 4 exit from the exit surfaces 5b of the prisms 5 without a change in the side-by-side direction but with a reduced distance between the optical axes.

Figure 4:
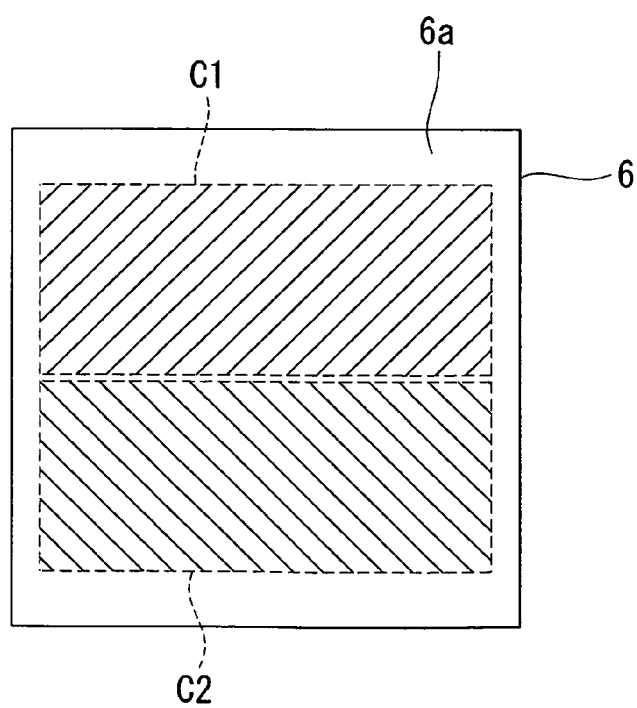
FIG. 4 is a front view showing an image-capturing surface of an image-capturing device that captures an image of light focused by the stereoscopic image-capturing objective optical system in FIG. 1.

The beams that exit from the second prism pair directly enter an image-capturing surface 6a of an image-capturing device 6. That is, as shown in FIG. 4, beams C1 and C2, which are formed to have a cross-sectional shape long in the side-by-side direction of the first lens groups 2 and short in the direction perpendicular thereto by the pair of second lens groups 4, enter the image-capturing surface 6a such that they are next to each other in the direction perpendicular to the side-by-side direction of the first lens groups 2.

An operation of the thus-configured stereoscopic image-capturing objective optical system 1 according to this embodiment will be described below.

In the stereoscopic image-capturing objective optical system 1 according to this embodiment, light emitted from a subject and entering the pair of first lens groups 2 having optical axes separated by a certain distance exits as substantially parallel parallax beams. The beams that exit from the first lens groups 2 enter the entrance surfaces 3a of the parallelogram prisms 3 constituting the first prism pair, disposed on the downstream side thereof.

Because the parallelogram prisms 3 each have the two reflecting surfaces 3c fabricated with precise parallelism, the beam that enters from the entrance surface 3a is reflected twice by the two reflecting surfaces 3c in the prism 3 and exits from the exit surface 3b. Because the exit surfaces 3b are arranged side-by-side in the direction perpendicular to the side-by-side direction of the entrance surfaces 3a, the two beams that exit from the two exit surfaces 3b are rotated by 90° from the side-by-side direction when they enter the two entrance surfaces 3a.

In this case, the distance between the center positions of the two entrance surfaces 3a and the distance between the center positions of the two exit surfaces 3b are both relatively large. Therefore, the two parallelogram prisms 3 can be disposed without interfering with each other, even if they are disposed obliquely with respect to the side-by-side direction of the entrance surfaces 3a such that the side-by-side direction of the optical axes is rotated by 90°.

Furthermore, the optical axes of the beams that exit from the exit surfaces 3b of the parallelogram prisms 3 are precisely parallel to the optical axes of the beams when entering the entrance surfaces 3a. In this case, in this embodiment, by using the parallelogram prisms 3, the parallelism between the two reflecting surfaces 3c is not affected by the mounting accuracy of the parallelogram prisms 3. Accordingly, even if there is an error in mounting the parallelogram prisms 3, the parallelism between the entrance optical axes and the exit optical axes can be precisely maintained.

Then, the two beams that exit from the exit surfaces 3b of the parallelogram prisms 3 enter the pair of second lens groups 4, where the beams are focused by the positive refractive power. Because one or more of the lenses in the second lens groups 4 has a toric surface, the two beams are converted into beams magnified by different magnifications in two directions perpendicular to each other and thus have a flat cross-section before entering the entrance surfaces 5a of the prisms 5 constituting the second prism pair.

In this case, in this embodiment, because the two parallax beams separated by a certain distance pass through the pair of second lens groups 4, a relatively large diameter of the beams can be ensured. Accordingly, the F number can be reduced to obtain a bright stereoscopic image.

Because the second prism pair is also composed of the two parallelogram prisms 5, the beams that enter from the entrance surfaces 5a are reflected twice by the two reflecting surfaces 5c in the prisms 5 and exit from the exit surfaces 5b. The optical axes of the beams that exit from the exit surfaces 5b of the parallelogram prisms 5 are precisely parallel to the optical axes of the beams when entering the entrance surfaces 5a. Thus, even if there is an error in mounting the parallelogram prisms 5, the parallelism between the entrance optical axes and the exit optical axes can be precisely maintained.

Furthermore, the long sides of the horizontally elongated rectangular exit surfaces 5b of the pair of second prisms 5 are disposed adjacent to each other to reduce the distance between the optical axes only in the direction perpendicular to the side-by-side direction of the entrance optical axes at the pair of first lens groups 2. This configuration enables the parallax beams to enter the adjacent areas of the image-capturing surface 6a of the image-capturing device 6 located downstream of the exit surfaces 5b and facing thereto, as shown in FIG. 4, and enables an image to be captured.

Although the two prisms 5 constituting the second prism pair are disposed such that the center positions of the exit surfaces 5b are close enough to each other in this case, because the prisms 5 reduce the distance between the optical axes only in one direction, they can be disposed without interfering with each other. Thus, by reducing the distance between the optical axes of the two beams with the second prism pair in this manner, stereoscopic image-capturing can be performed using the small image-capturing device 6.

As has been described above, with the objective optical system 1 for stereoscopic observation according to this embodiment, there is no need to precisely adjust the angle of the mirrors compared with a conventional optical system employing a plurality of mirrors for reflection, and thus, the prisms 3 and 5 can be easily positioned. Accordingly, a precise position-adjusting mechanism is unnecessary, which makes the system compact. This also reduces the diameter of an insertion portion of an endoscope having the objective optical system 1 for stereoscopic observation according to this embodiment at the tip thereof.

Furthermore, because the parallelism between the entrance optical axes and the exit optical axes of the parallelogram prisms 3 and 5 is not degraded even with easy positioning, tilting of an image at the image-capturing surface 6a can be prevented.

Furthermore, even if the diameter of the beams is increased, the beams can be guided to the image-capturing surface 6a without interfering with each other. This leads to an advantage in that the F number can be reduced to capture a bright stereoscopic image.

In this embodiment, the side-by-side direction of the two beams is rotated by 90° in the first prisms 3 and is not rotated in the second prisms 5. Instead of this, the first and second prisms 3 and 5 may share the rotation in the side-by-side direction to achieve a total rotation angle of 90°. In this case, it is preferable that the first prisms 3 be rotated by a larger angle than the second prisms 5. The reason for this is that, because the second prisms 5 have the exit surfaces 5a that are close to each other, the prisms 5 interfere with each other when the side-by-side direction is rotated by a larger angle, requiring removal of the interfering portions and making the shape of the prisms complex.

Figure 5:
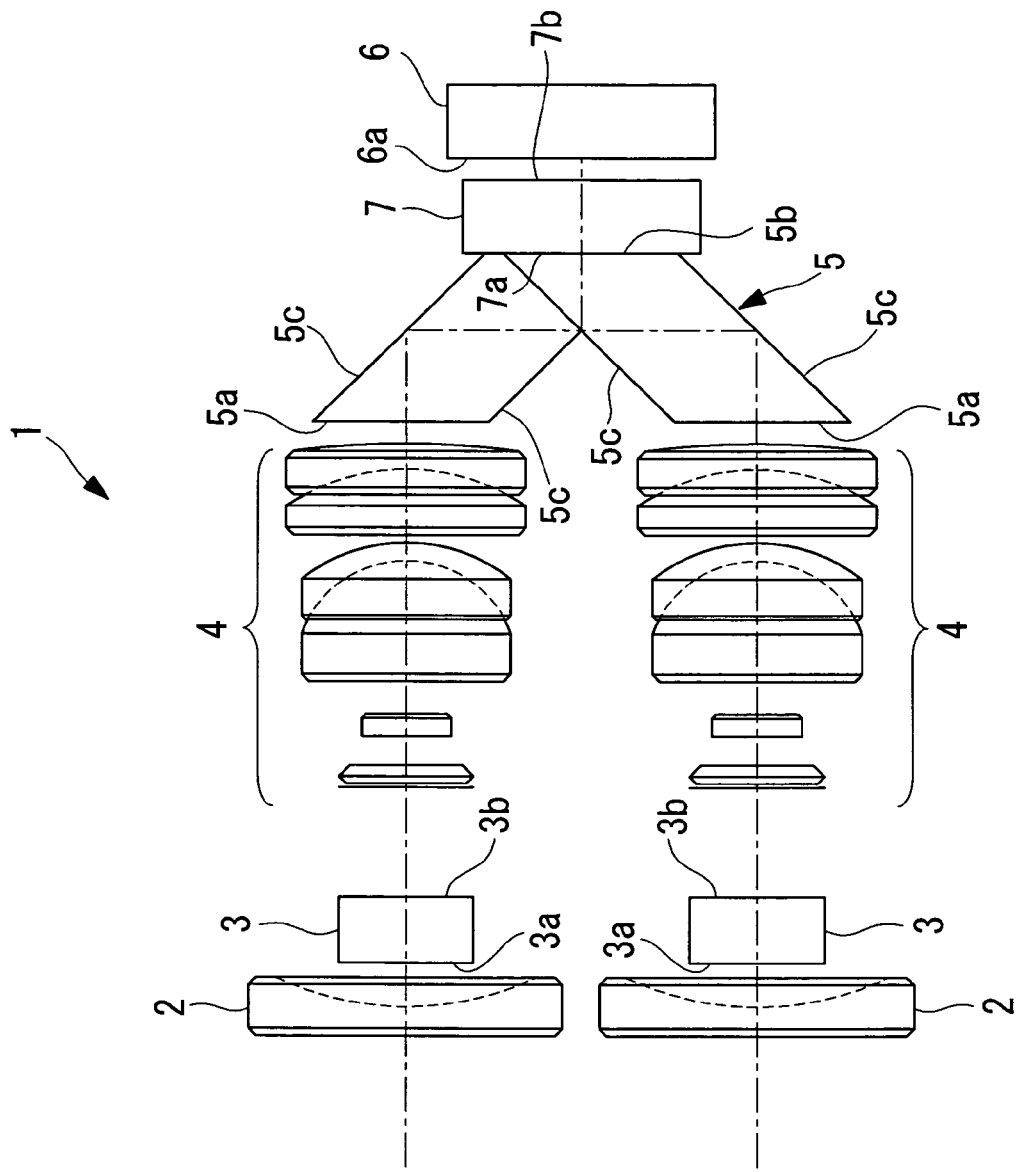
FIG. 5 is an (XZ) plan view of a modification of the stereoscopic image-capturing objective optical system in FIG. 1.
Figure 6:
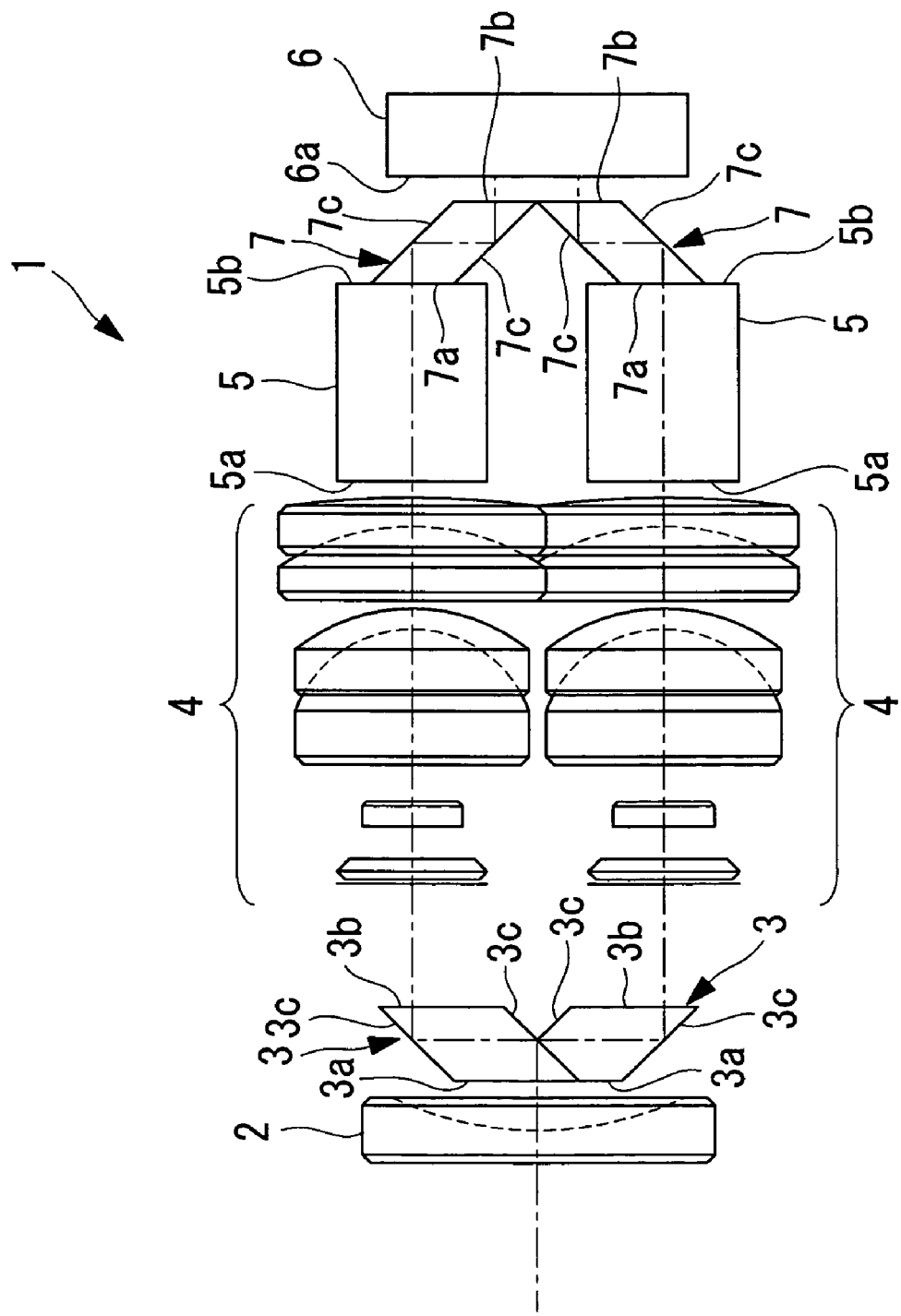
FIG. 6 is a (YZ) side view of the stereoscopic image-capturing objective optical system in FIG. 5.
Figure 7:
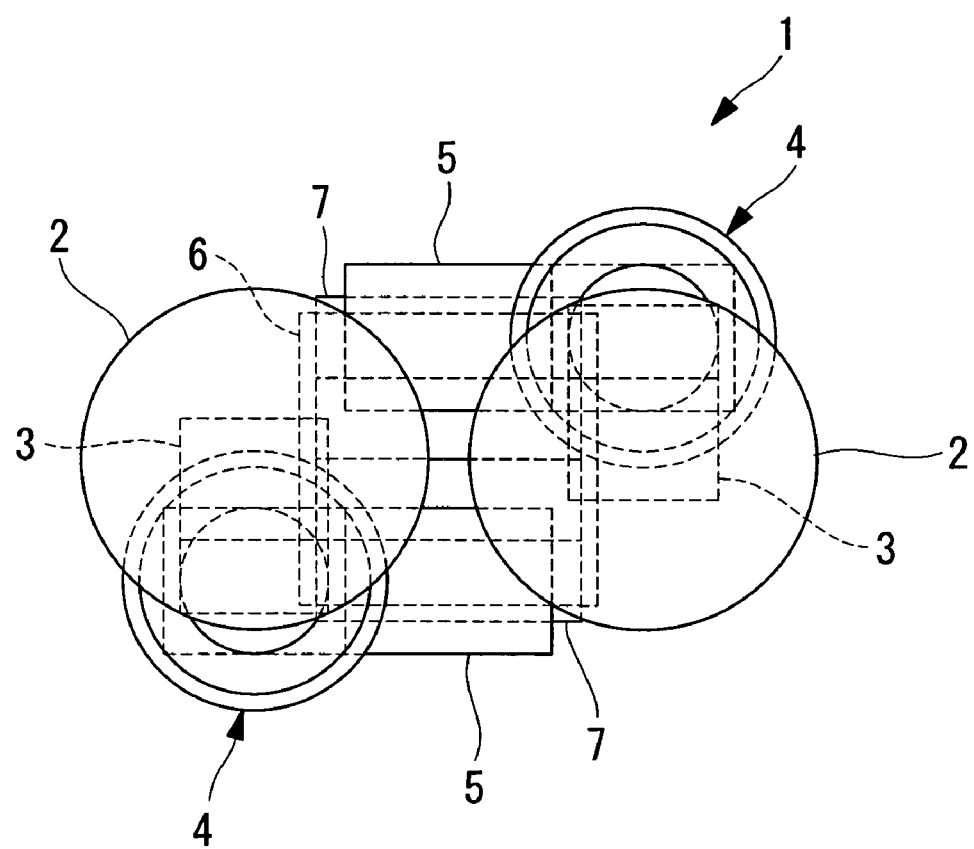
FIG. 7 is a front view of the stereoscopic image-capturing objective optical system in FIG. 5, viewed from the object side.

Furthermore, in this embodiment, although the first and second prisms 3 and 5 are each formed of one prism pair, they may be each formed of two or more prism pairs, as shown in FIGS. 5 to 7. In the example shown in FIGS. 5 to 7, the prisms 3 constituting the first prism pair shift the beams in the direction perpendicular to the side-by-side direction of the two beams, thereby rotating the side-by-side direction by an angle smaller than 90°. Furthermore, the pair of second prisms 5 and a pair of third prisms 7 employed herein shift the beams in the direction parallel to and in the direction perpendicular to the side-by-side direction of the two beams before entering the first prisms 3, respectively.

By doing so, similarly to the above-described embodiment, it is possible to employ the third prisms 7 that have exit surfaces 7*b* facing the image-capturing surface 6*a* and have a function only to reduce the distance between the beams in the direction perpendicular to the side-by-side direction of the optical axes that enters the pair of first lens groups 2, which can simplify the configuration. Furthermore, even if the positions of two reflecting surfaces 7*c* of the parallelogram prism 7 are shifted as a result of them being easily positionable, the parallelism between the entrance optical axes and the exit optical axes of the parallelogram prism 7 is not degraded. Thus, tilting of an image at the image-capturing surface 6*a* can be prevented.

Note that the configuration of the prisms is not limited to that in the above-described embodiment, and a modification is possible such that the first prisms 3 shift the beams in the direction perpendicular to the side-by-side direction of the two beams and the second prisms 5 shift the two beams such that the beams are arranged side-by-side in the direction perpendicular to the side-by-side direction thereof before entering the first prisms 3.

EXAMPLES

Now, examples of the stereoscopic image-capturing objective optical system 1 according to this embodiment will be described below with reference to the drawings. In each example, among the two pairs of lens groups 2 and 4 and the two pairs of prisms 3 and 5 (or the three pairs of prisms 3, 5, and 7), drawings and lens data are shown with respect to one of the lens groups 2 and 4 and prisms 3 and 5 (or one of the prisms 3, 5, and 7), and the description of the other of the lens groups 2 and 4 and the prisms 3 and 5 will be omitted.

Example 1

Figure 8A:
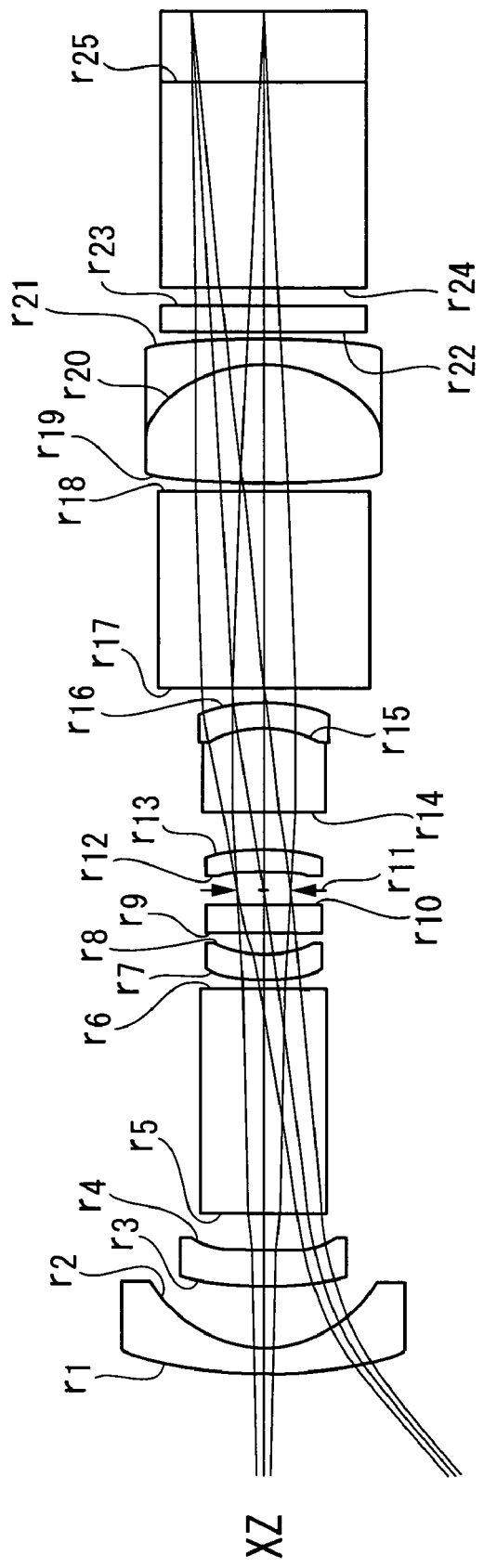
FIG. 8A is a diagram showing the lens configuration along the XZ plane, showing a first example of this embodiment.
Figure 8B:
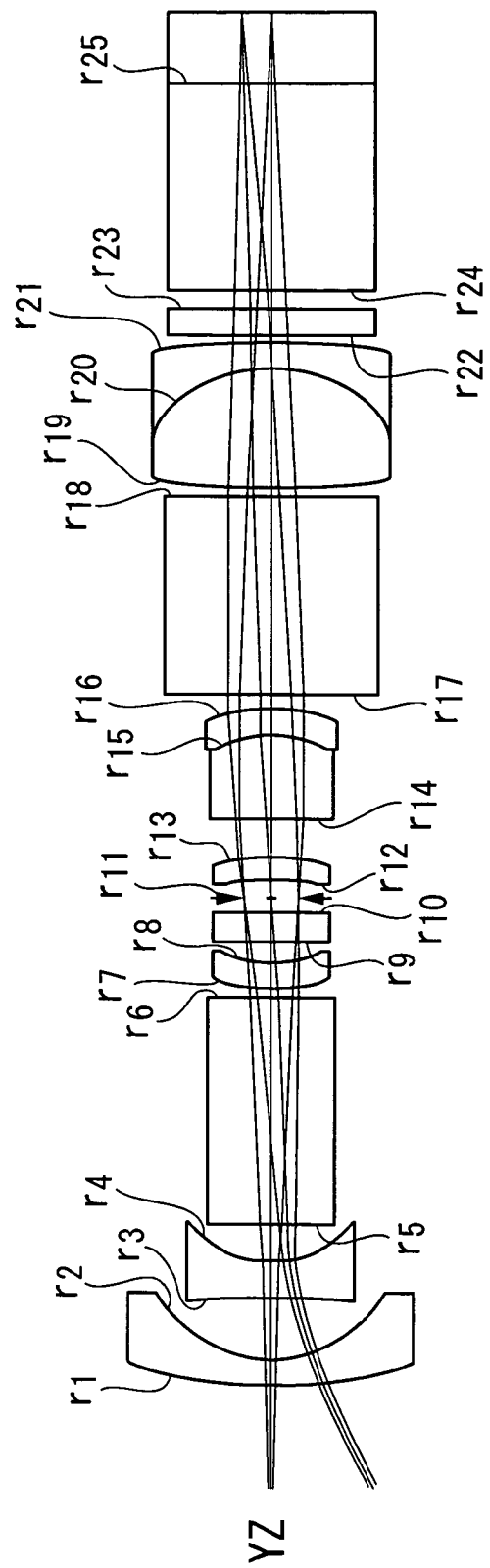
FIG. 8B is a diagram showing the lens configuration along the YZ plane, showing the first example of this embodiment.

Lens configuration diagrams of the stereoscopic image-capturing objective optical system 1 according to Example 1 are shown in FIGS. 8A and 8B, and the lens data thereof are shown below. Furthermore, aberration diagrams of the objective lens of this example are shown in FIGS. 9A to 9E. FIG. 8A is a lens configuration diagram along the XZ plane, and FIG. 8B is a lens configuration diagram along the YZ plane.

Figure 9A:
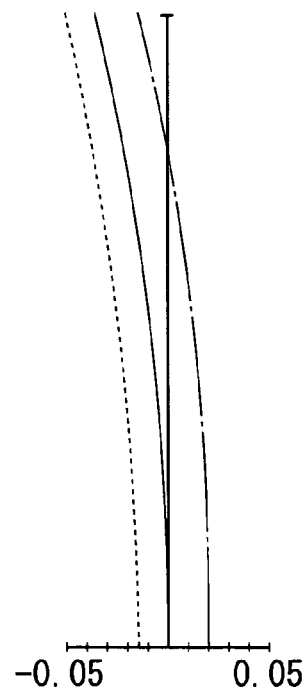
FIG. 9A is a spherical aberration diagram in the XZ cross-section of the lens configuration shown in FIGS. 8A and 8B.
Figure 9B:
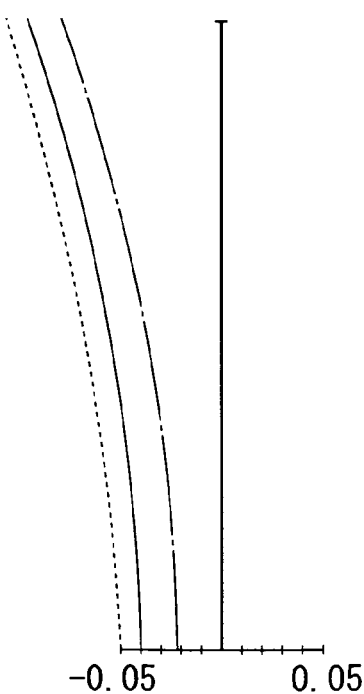
FIG. 9B is a spherical aberration diagram in the YZ cross-section of the lens configuration shown in FIGS. 8A and 8B.
Figure 9C:
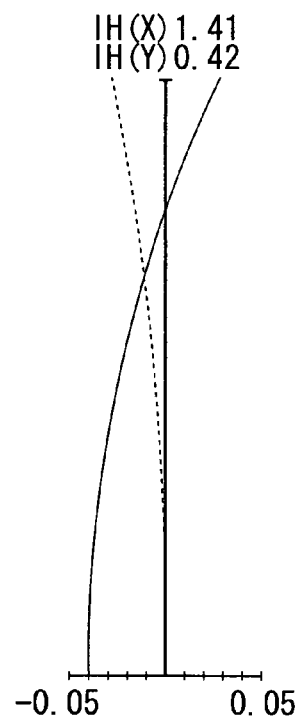
FIG. 9C is an aberration diagram showing astigmatism with the lens configuration shown in FIGS. 8A and 8B, the solid line corresponding to the sagittal direction (YZ direction), and the broken line corresponding to the meridional direction (XZ direction).
Figure 9D:
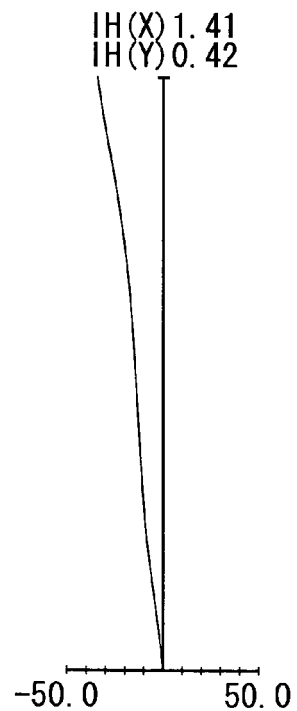
FIG. 9D is a distortion diagram in the diagonal direction of the lens configuration shown in FIGS. 8A and 8B.
Figure 9E:
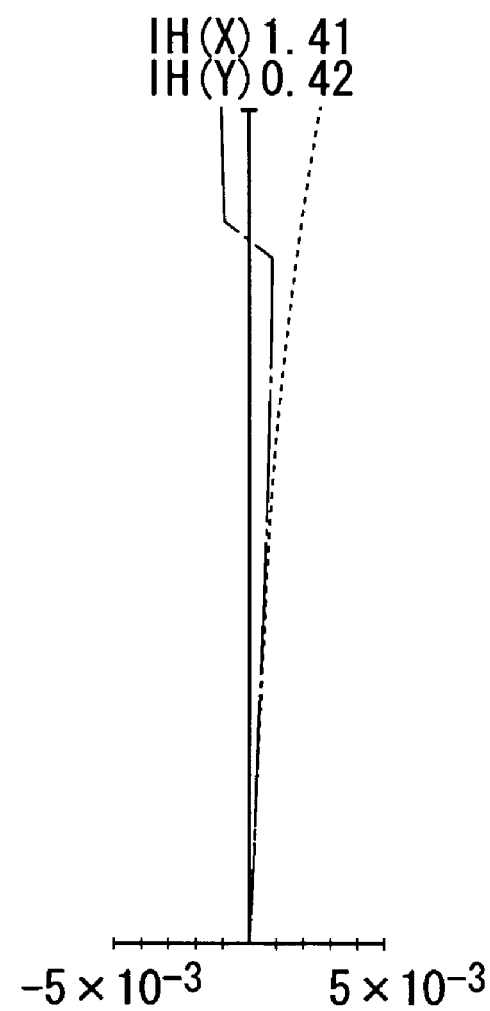
FIG. 9E is a magnification chromatic aberration diagram in the diagonal direction of the lens configuration shown in FIGS. 8A and 8B.

FIG. 9A is a spherical aberration diagram in the XZ cross-section, FIG. 9B is a spherical aberration diagram in the YZ cross-section, and FIG. 9C is a diagram of astigmatism, in which the solid line represents aberration in the sagittal direction (YZ direction), and the broken line represents aberration in the meridional direction (XZ direction), FIG. 9D is a distortion diagram in the diagonal direction, and FIG. 9E is a magnification chromatic aberration diagram in the diagonal direction. Furthermore, in FIGS. 9A and 9E, the solid line represents aberration at the e-line (546.07 nm), the one-dot chain line represents aberration at the F-line (486.13 nm), and the broken line represents aberration at the C-line (656.27 nm).

| Surface Data | | | | |
|---|---|---|---|---|
| surface number | r | d | ne | vd |
| object plane | ∞ | 26 | | |
| 1 | 6.4 | 0.388 | 1.88815 | 40.76 |
| 2 | 1.89 | 0.836 | | |
| 3$ | 5.833 | 0.47 | 2.01169 | 28.27 |
| 4$ | 3.016 | 0.537 | | |
| 5 | ∞ | 3.066 | 1.77621 | 49.6 |
| 6 | ∞ | 0.135 | | |
| 7$ | 2.254 | 0.339 | 1.77621 | 49.6 |
| 8$ | 1.624 | 0.321 | | |
| 9 | ∞ | 0.4 | 1.77621 | 49.6 |
| 10 | ∞ | 0.2 | | |
| 11 (stop) | ∞ | 0.213 | | |
| 12 | −11.144 | 0.342 | 1.93429 | 18.9 |
| 13 | −3.629 | 0.521 | | |
| 14 | 11.974 | 1.178 | 1.48915 | 70.23 |
| 15 | −1.646 | 0.389 | 1.85504 | 23.78 |
| 16 | −2.247 | 0.11 | | |
| 17 | ∞ | 2.793 | 1.88815 | 40.76 |
| 18 | ∞ | 0.11 | | |
| 19 | 10.8766 | 1.632 | 1.77621 | 49.6 |
| 20 | −2.109 | 0.318 | 1.93429 | 18.9 |
| 21 | −24.357 | 0.107 | | |
| 22 | ∞ | 0.376 | 1.51564 | 75 |
| 23 | ∞ | 0.218 | | |
| 24 | ∞ | 2.8 | 1.51825 | 64.14 |
| 25 | ∞ | 0.97 | 1.50801 | 60 |
| image plane | ∞ | 0 | | |

| Aspherical Surface Data | | |
|---|---|---|
| | RDX | RDY |
| third surface TOC | 5.833 | −9.04 |
| fourth surface TOC | 3.016 | 1.478 |
| seventh surface TOC | 2.254 | 1.502 |
| eighth surface TOC | 1.624 | 1.354 |

Example 2

Figure 10A:
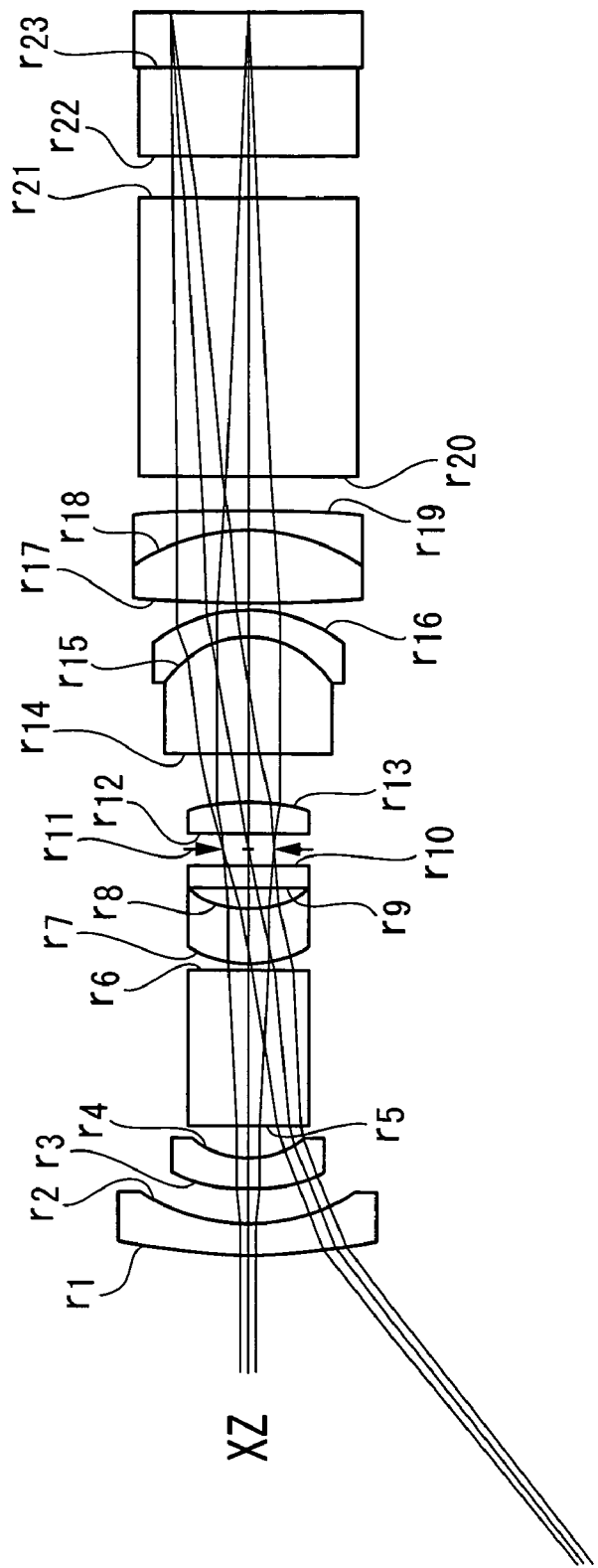
FIG. 10A is a diagram showing the lens configuration along the XZ plane, showing a second example of this embodiment.
Figure 10B:
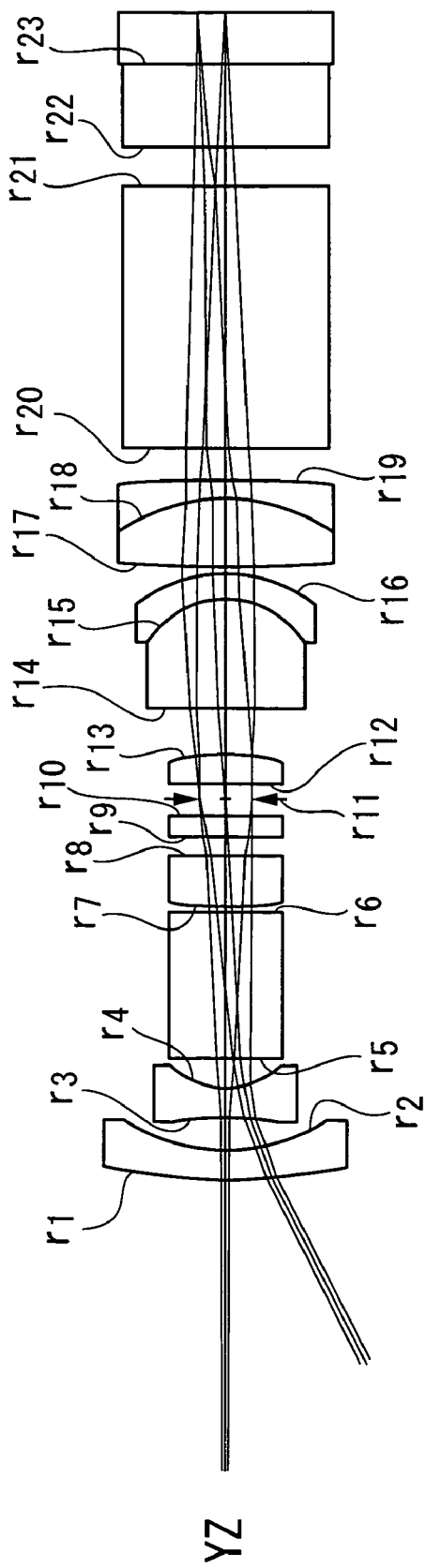
FIG. 10B is a diagram showing the lens configuration along the YZ plane, showing the second example of this embodiment.

Lens configuration diagrams of the stereoscopic image-capturing objective optical system according to Example 2 are shown in FIGS. 10A and 10B, and the lens data thereof are shown below. Furthermore, aberration diagrams of the objective lens of this example are shown in FIGS. 11A to 11E. FIG. 10A is a lens configuration diagram along the XZ plane, and FIG. 10B is a lens configuration diagram along the YZ plane.

Figure 11A:
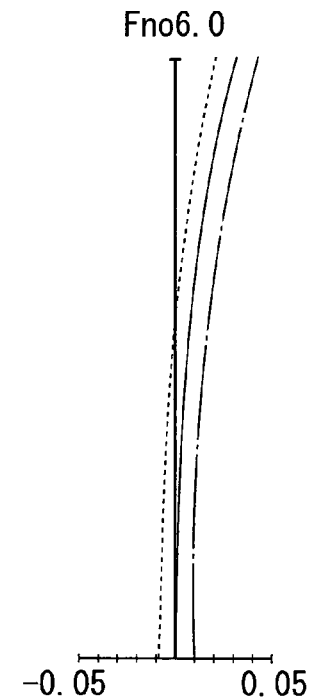
FIG. 11A is a spherical aberration diagram in the XZ cross-section of the lens configuration shown in FIGS. 10A and 10B.
Figure 11B:
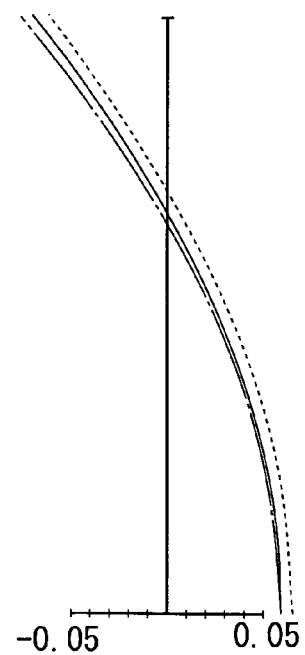
FIG. 11B is a spherical aberration diagram in the YZ cross-section of the lens configuration shown in FIGS. 10A and 10B.
Figure 11C:
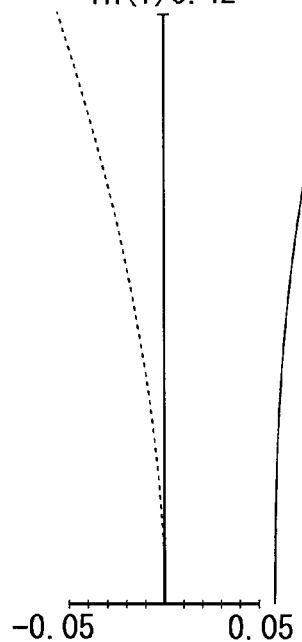
FIG. 11C is an aberration diagram showing astigmatism with the lens configuration shown in FIGS. 10A and 10B, the solid line corresponding to the sagittal direction (YZ direction), and the broken line corresponding to the meridional direction (XZ direction).
Figure 11D:
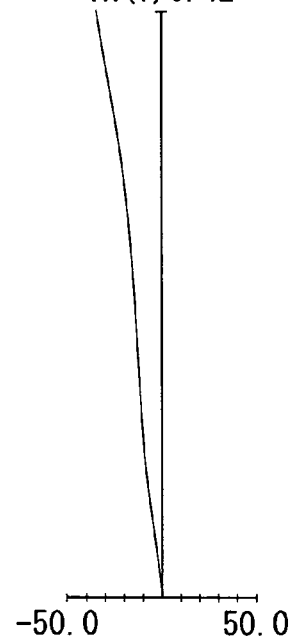
FIG. 11D is a distortion diagram in the diagonal direction of the lens configuration shown in FIGS. 10A and 10B.
Figure 11E:
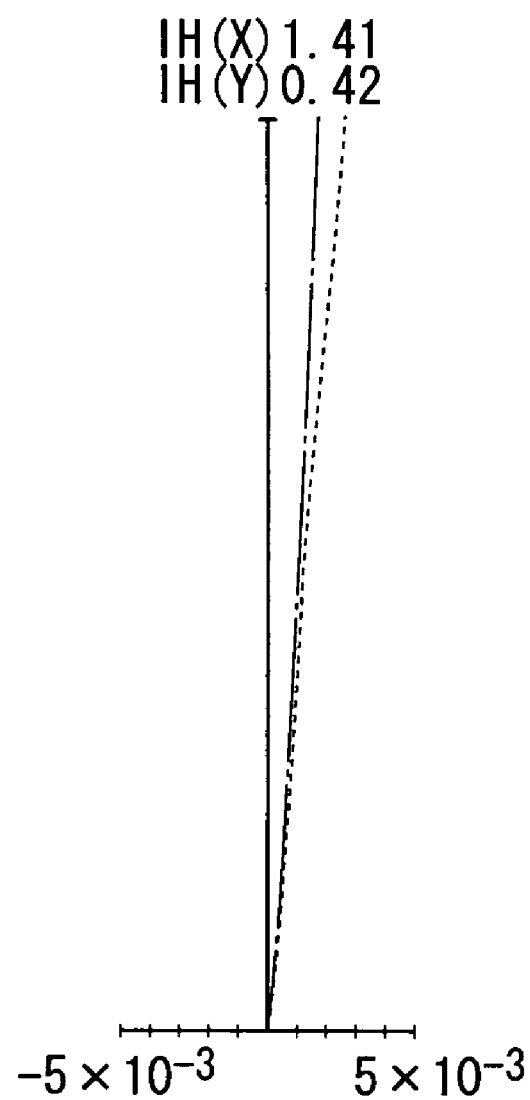
FIG. 11E is a magnification chromatic aberration diagram in the diagonal direction of the lens configuration shown in FIGS. 10A and 10B.

FIG. 11A is a spherical aberration diagram in the XZ cross-section, FIG. 11B is a spherical aberration diagram in the YZ cross-section, and FIG. 11C is a diagram of astigmatism, in which the solid line represents aberration in the sagittal direction (YZ direction), and the broken line represents aberration in the meridional direction (XZ direction), FIG. 11D is a distortion diagram in the diagonal direction, and FIG. 11E is a magnification chromatic aberration diagram in the diagonal direction. Furthermore, in FIGS. 11A and 11E, the solid line represents aberration at the e-line (546.07 nm), the one-dot chain line represents aberration at the F-line (486.13 nm), and the broken line represents aberration at the C-line (656.27 nm).

| Surface Data | | | | |
|---|---|---|---|---|
| surface number | r | d | ne | vd |
| object plane | ∞ | 26 | | |
| 1 | 12.747 | 0.388 | 1.88815 | 40.76 |
| 2 | 2.57 | 0.435 | | |

-continued

| | | | | |
|---|---|---|---|---|
| 3$ | 2.779 | 0.421 | 2.01169 | 28.27 |
| 4$ | 1.382 | 0.411 | | |
| 5 | ∞ | 2 | 1.77621 | 49.6 |
| 6 | ∞ | 0.078 | | |
| 7$ | 1.676 | 0.672 | 1.77621 | 49.6 |
| 8$ | 1.348 | 0.287 | | |
| 9 | ∞ | 0.3 | 1.51825 | 64.14 |
| 10 | ∞ | 0.2 | | |
| 11 (stop) | ∞ | 0.19 | | |
| 12 | −33.73 | 0.405 | 1.93429 | 18.9 |
| 13 | −3.05 | 0.628 | | |
| 14 | 29.794 | 1.506 | 1.48915 | 70.23 |
| 15 | −1.292 | 0.378 | 1.85504 | 23.78 |
| 16 | −1.895 | 0.098 | | |
| 17 | 19.637 | 0.924 | 1.77621 | 49.6 |
| 18 | −2.655 | 0.267 | 1.93429 | 18.9 |
| 19 | −29.47 | 0.418 | | |
| 20 | ∞ | 3.56 | 1.88815 | 40.76 |
| 21 | ∞ | 0.565 | | |
| 22 | ∞ | 1.1 | 1.51825 | 64.14 |
| 23 | ∞ | 0.7 | 1.50801 | 60 |
| image plane | ∞ | 0 | | |

Aspherical Surface Data

| | RDX | RDY |
|---|---|---|
| third surface TOC | 2.779 | −12.761 |
| fourth surface TOC | 1.382 | 1.159 |
| seventh surface TOC | 1.676 | 12.56 |
| eighth surface TOC | 1.348 | 6.743 |

Example 3

Figure 12A:
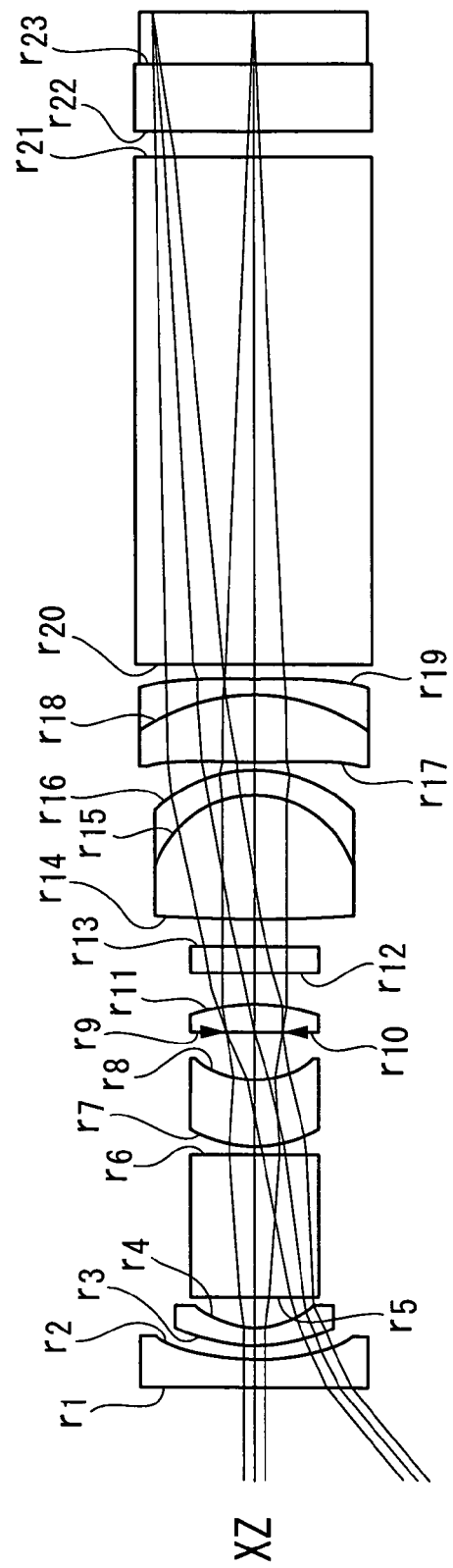
FIG. 12A is a diagram showing the lens configuration along the XZ plane, showing a third example of this embodiment.
Figure 12B:
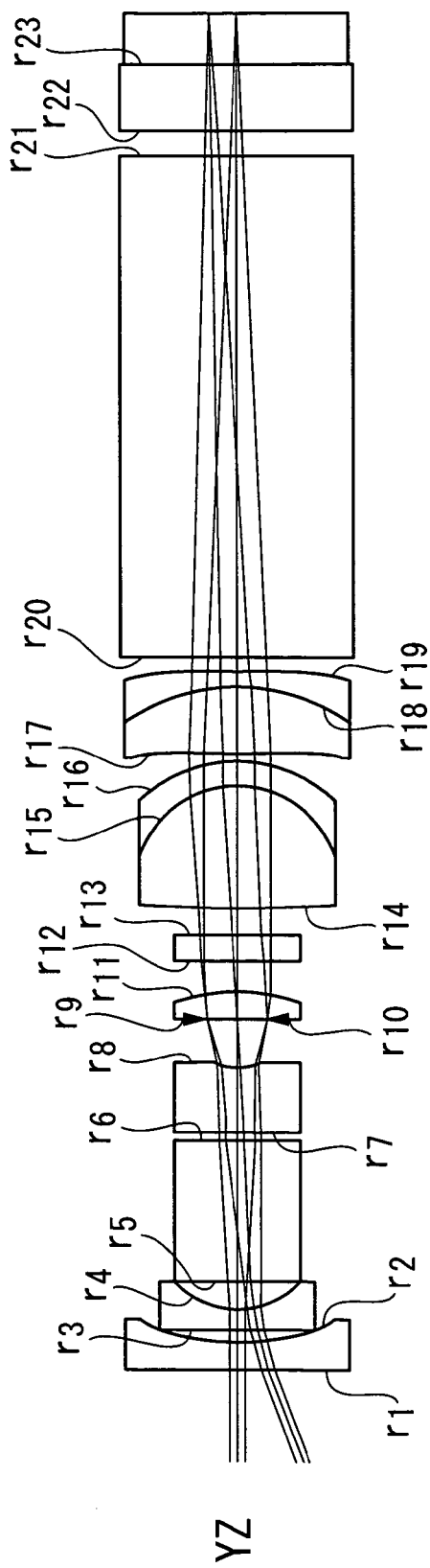
FIG. 12B is a diagram showing the lens configuration along the YZ plane, showing the third example of this embodiment.

Lens configuration diagrams of the stereoscopic image-capturing objective optical system according to Example 3 are shown in FIGS. 12A and 12B, and the lens data thereof are shown below. Furthermore, aberration diagrams of the objective lens of this example are shown in FIGS. 13A to 13E. FIG. 12A is a lens configuration diagram along the XZ plane, and FIG. 12B is a lens configuration diagram along the YZ plane.

Figure 13A:
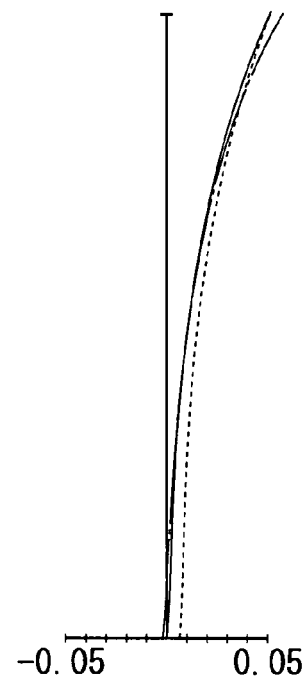
FIG. 13A is a spherical aberration diagram in the XZ cross-section of the lens configuration shown in FIGS. 12A and 12B.
Figure 13B:
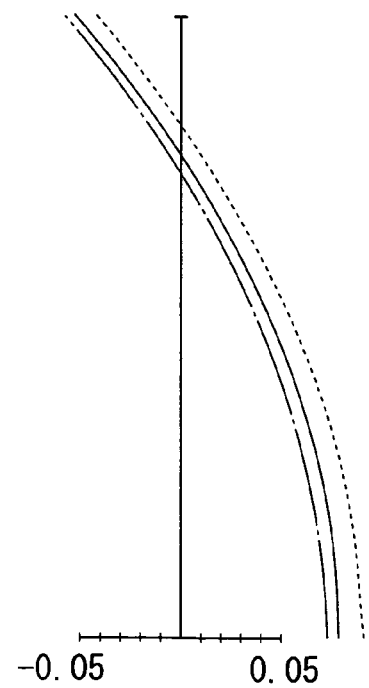
FIG. 13B is a spherical aberration diagram in the YZ cross-section of the lens configuration shown in FIGS. 12A and 12B.
Figure 13C:
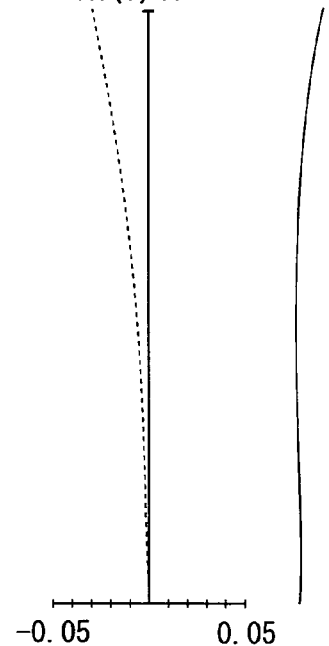
FIG. 13C is an aberration diagram showing astigmatism with the lens configuration shown in FIGS. 12A and 12B, the solid line corresponding to the sagittal direction (YZ direction), and the broken line corresponding to the meridional direction (XZ direction).
Figure 13D:
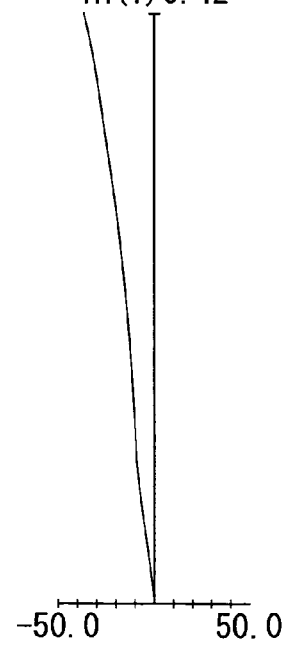
FIG. 13D is a distortion diagram in the diagonal direction of the lens configuration shown in FIGS. 12A and 12B.
Figure 13E:
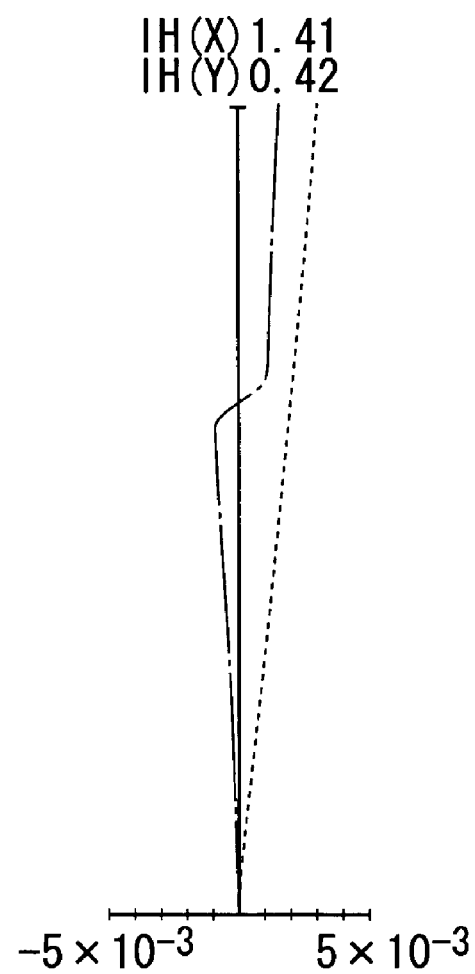
FIG. 13E is a magnification chromatic aberration diagram in the diagonal direction of the lens configuration shown in FIGS. 12A and 12B.

FIG. 13A is a spherical aberration diagram in the XZ cross-section, FIG. 13B is a spherical aberration diagram in the YZ cross-section, and FIG. 13C is a diagram of astigmatism, in which the solid line represents aberration in the sagittal direction (YZ direction), and the broken line represents aberration in the meridional direction (XZ direction), FIG. 13D is a distortion diagram in the diagonal direction, and FIG. 13E is a magnification chromatic aberration diagram in the diagonal direction. Furthermore, in FIGS. 13A and 13E, the solid line represents aberration at the e-line (546.07 nm), the one-dot chain line represents aberration at the F-line (486.13 nm), and the broken line represents aberration at the C-line (656.27 nm).

Surface Data

| surface number | r | d | ne | vd |
|---|---|---|---|---|
| object plane | ∞ | 29.73 | | |
| 1 | 29.785 | 0.444 | 1.88815 | 40.76 |
| 2 | 3.304 | 0.18 | | |
| 3$ | 2.45 | 0.245 | 2.01169 | 28.27 |
| 4$ | 1.347 | 0.405 | | |
| 5 | ∞ | 2 | 1.77621 | 49.6 |
| 6 | ∞ | 0.101 | | |
| 7$ | 1.781 | 0.92 | 1.77621 | 49.6 |
| 8$ | 1.391 | 0.66 | | |
| 9 (stop) | ∞ | 0.019 | | |
| 10 | −6.261 | 0.369 | 1.93429 | 18.9 |
| 11 | −2.23 | 0.44 | | |
| 12 | ∞ | 0.343 | 1.51825 | 64.14 |
| 13 | ∞ | 0.373 | | |
| 14 | 129.693 | 1.673 | 1.48915 | 70.23 |
| 15 | −1.473 | 0.354 | 1.85504 | 23.78 |
| 16 | −2.037 | 0.101 | | |
| 17 | −40.113 | 0.928 | 1.77621 | 49.6 |
| 18 | −2.936 | 0.243 | 1.93429 | 18.9 |
| 19 | −12.017 | 0.198 | | |
| 20 | ∞ | 6.96 | 2.01169 | 28.27 |
| 21 | ∞ | 0.369 | | |
| 22 | ∞ | 0.9 | 1.51825 | 64.14 |
| 23 | ∞ | 0.7 | 1.50801 | 60 |
| image plane | ∞ | 0 | | |

Aspherical Surface Data

| | RDX | RDY |
|---|---|---|
| third surface TOC | 2.45 | 27.302 |
| fourth surface TOC | 1.347 | 1.194 |
| seventh surface TOC | 1.781 | 37.743 |
| eighth surface TOC | 1.391 | 7.041 |

Example 4

Figure 14A:
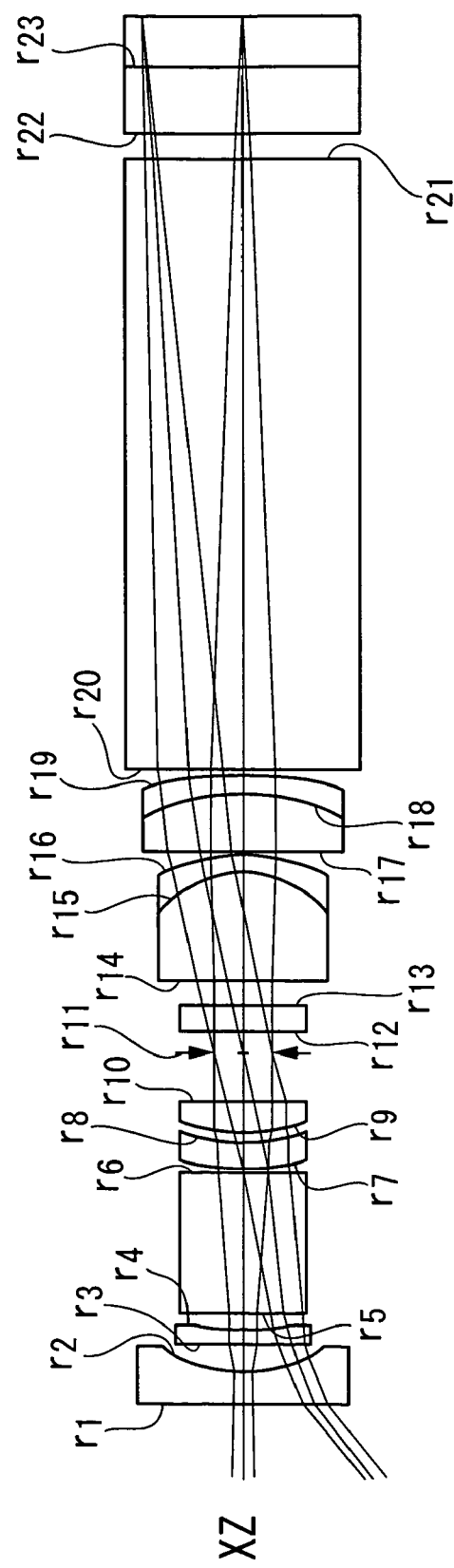
FIG. 14A is a diagram showing the lens configuration along the XZ plane, showing a fourth example of this embodiment.
Figure 14B:
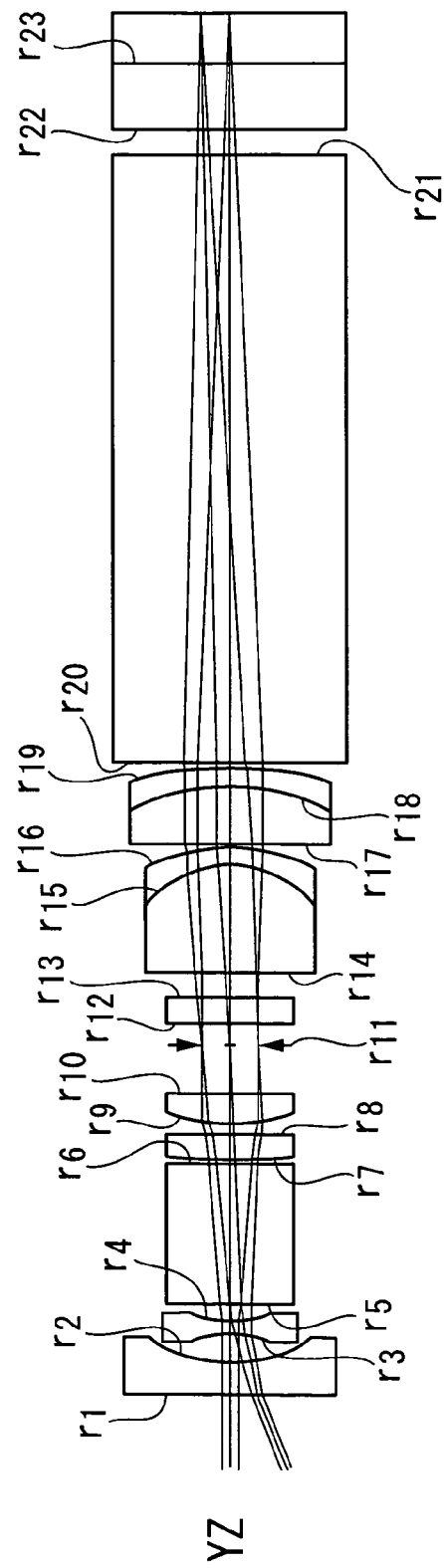
FIG. 14B is a diagram showing the lens configuration along the YZ plane, showing the fourth example of this embodiment.

Lens configuration diagrams of the stereoscopic image-capturing objective optical system 1 according to Example 4 are shown in FIGS. 14A and 14B, and the lens data thereof are shown below. Furthermore, aberration diagrams of the objective lens of this example are shown in FIGS. 15A to 15E. FIG. 14A is a lens configuration diagram along the XZ plane, and FIG. 14B is a lens configuration diagram along the YZ plane.

Figure 15A:
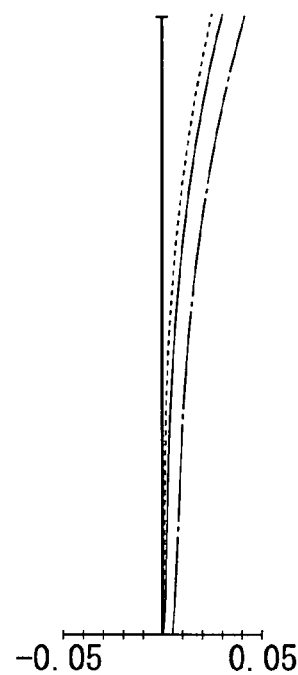
FIG. 15A is a spherical aberration diagram in the XZ cross-section of the lens configuration shown in FIGS. 14A and 14B.
Figure 15B:
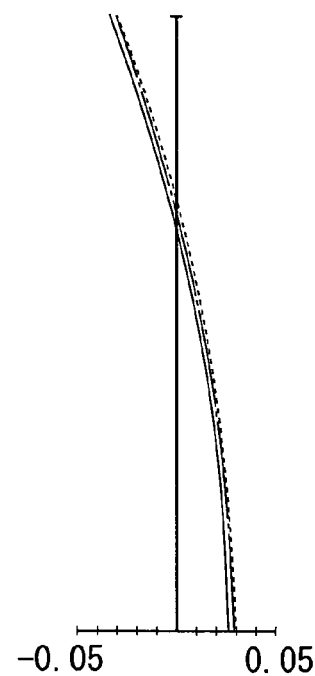
FIG. 15B is a spherical aberration diagram in the YZ cross-section of the lens configuration shown in FIGS. 14A and 14B.
Figure 15C:
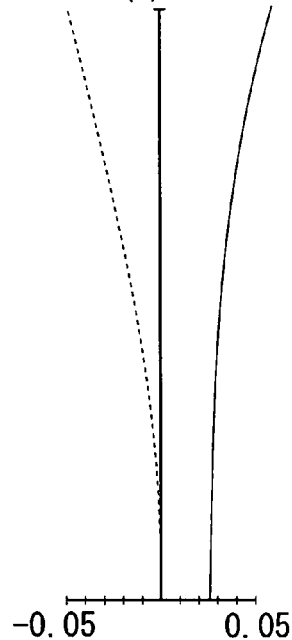
FIG. 15C is an aberration diagram showing astigmatism with the lens configuration shown in FIGS. 14A and 14B, the solid line corresponding to the sagittal direction (YZ direction), and the broken line corresponding to the meridional direction (XZ direction).
Figure 15D:
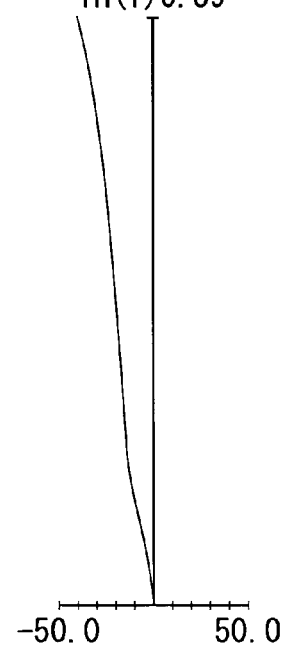
FIG. 15D is a distortion diagram in the diagonal direction of the lens configuration shown in FIGS. 14A and 14B.
Figure 15E:
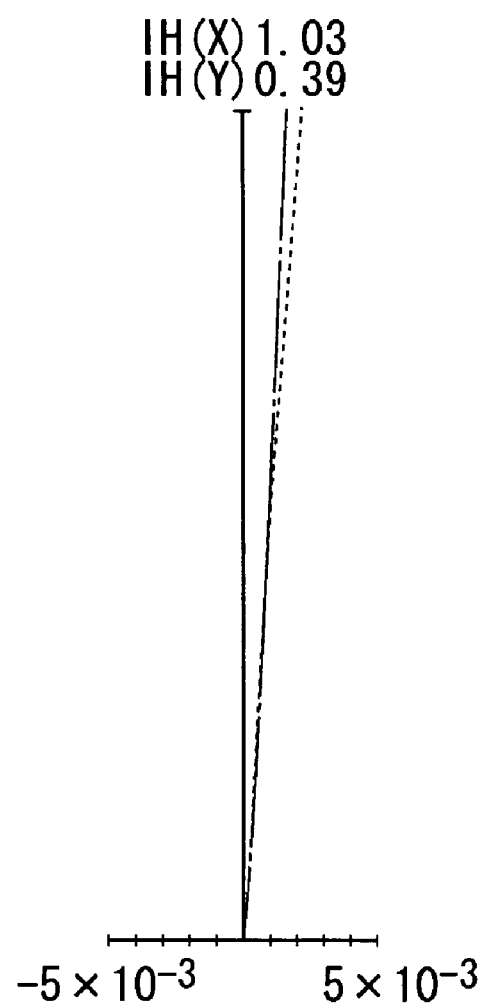
FIG. 15E is a magnification chromatic aberration diagram in the diagonal direction of the lens configuration shown in FIGS. 14A and 14B.

FIG. 15A is a spherical aberration diagram in the XZ cross-section, FIG. 15B is a spherical aberration diagram in the YZ cross-section, and FIG. 15C is a diagram of astigmatism, in which the solid line represents aberration in the sagittal direction (YZ direction), and the broken line represents aberration in the meridional direction (XZ direction), FIG. 15D is a distortion diagram in the diagonal direction, and FIG. 15E is a magnification chromatic aberration diagram in the diagonal direction. Furthermore, in FIGS. 15A and 15E, the solid line represents aberration at the e-line (546.07 nm), the one-dot chain line represents aberration at the F-line (486.13 nm), and the broken line represents aberration at the C-line (656.27 nm).

Surface Data

| surface number | r | d | ne | vd |
|---|---|---|---|---|
| object plane | ∞ | 29.7259 | | |
| 1 | ∞ | 0.444 | 1.88815 | 40.76 |
| 2 | 2.155 | 0.393 | | |
| 3$ | 15.248 | 0.207 | 2.01169 | 28.27 |
| 4$ | 4.296 | 0.195 | | |
| 5 | ∞ | 2 | 1.77621 | 49.6 |
| 6 | ∞ | 0.069 | | |
| 7$ | 5.636 | 0.347 | 1.77621 | 49.6 |
| 8$ | 2.994 | 0.155 | | |
| 9 | 3.498 | 0.409 | 1.93429 | 18.9 |
| 10 | −13.631 | 0.67 | | |
| 11 (stop) | ∞ | 0.324 | | |
| 12 | ∞ | 0.343 | 1.51825 | 64.14 |
| 13 | ∞ | 0.329 | | |
| 14 | 129.743 | 1.485 | 1.48915 | 70.23 |
| 15 | −1.463 | 0.228 | 1.85504 | 23.78 |
| 16 | −2.565 | 0.048 | | |
| 17 | −84.942 | 0.808 | 1.77621 | 49.6 |
| 18 | −3.054 | 0.263 | 1.93429 | 18.9 |

-continued

| 19 | −4.823 | 0.057 | | |
| 20 | ∞ | 8.4 | 2.01169 | 28.27 |
| 21 | ∞ | 0.369 | | |
| 22 | ∞ | 0.9 | 1.51825 | 64.14 |
| 23 | ∞ | 0.7 | 1.50801 | 60 |
| image plane | ∞ | 0 | | |

Aspherical Surface Data

| | RDX | RDY |
| --- | --- | --- |
| third surface TOC | 15.248 | −2.229 |
| fourth surface TOC | 4.296 | 1.829 |
| seventh surface TOC | 5.636 | 39.815 |
| eighth surface TOC | 2.994 | 46.6 |

Example 5

Figure 16A:
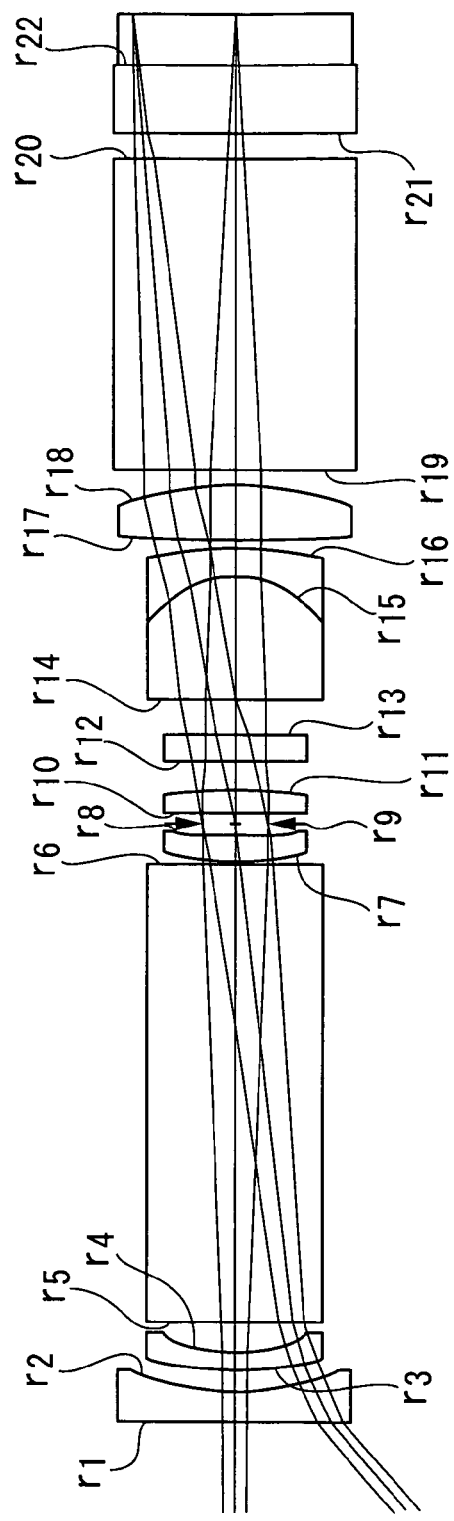
FIG. 16A is a diagram showing the lens configuration along the XZ plane, showing a fifth example of this embodiment.
Figure 16B:
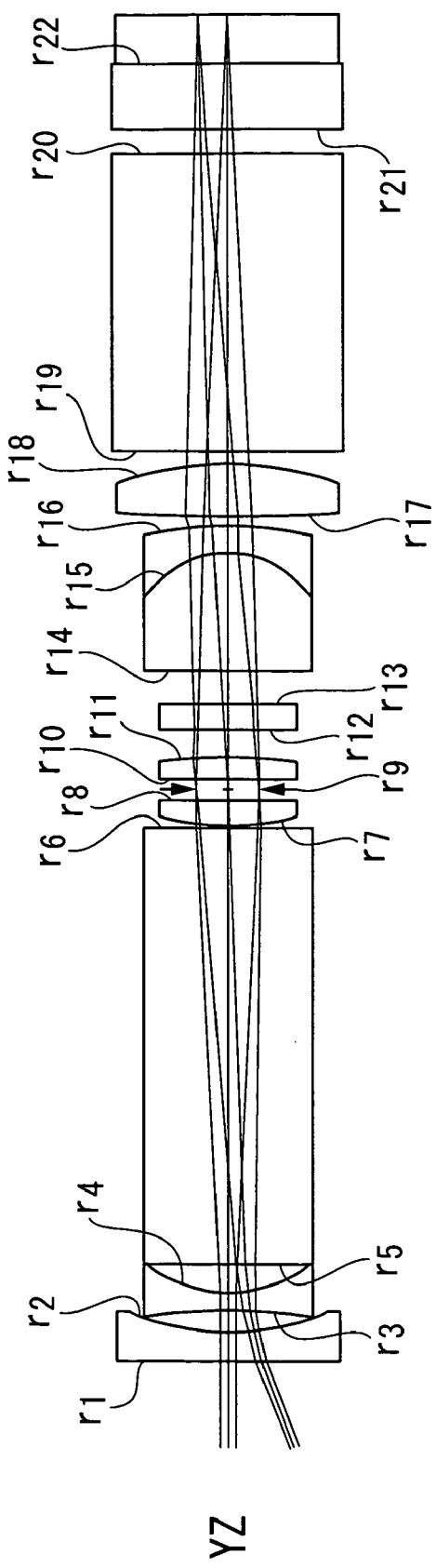
FIG. 16B is a diagram showing the lens configuration along the YZ plane, showing the fifth example of this embodiment.

Lens configuration diagrams of the stereoscopic image-capturing objective optical system 1 according to Example 5 are shown in FIGS. 16A and 16B, and the lens data thereof are shown below. Furthermore, aberration diagrams of the objective lens of this example are shown in FIGS. 17A to 17E. FIG. 16A is a lens configuration diagram along the XZ plane, and FIG. 16B is a lens configuration diagram along the YZ plane.

Figure 17A:
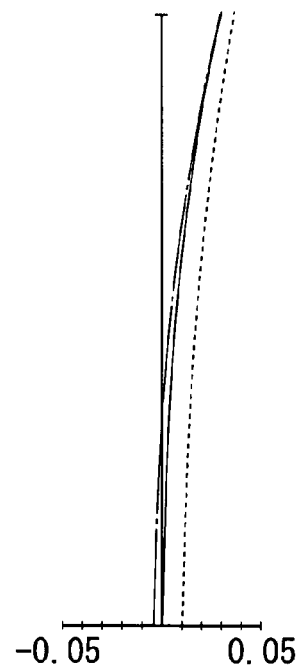
FIG. 17A is a spherical aberration diagram in the XZ cross-section of the lens configuration shown in FIGS. 16A and 16B.
Figure 17B:
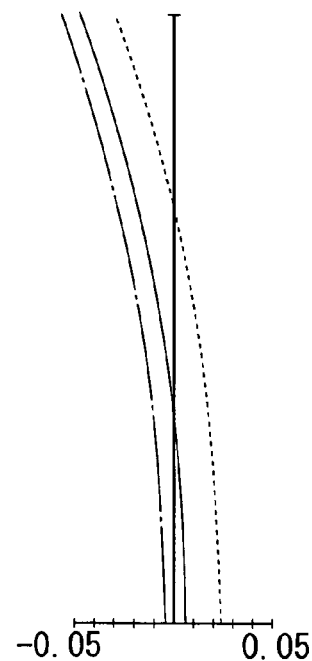
FIG. 17B is a spherical aberration diagram in the YZ cross-section of the lens configuration shown in FIGS. 16A and 16B.
Figure 17C:
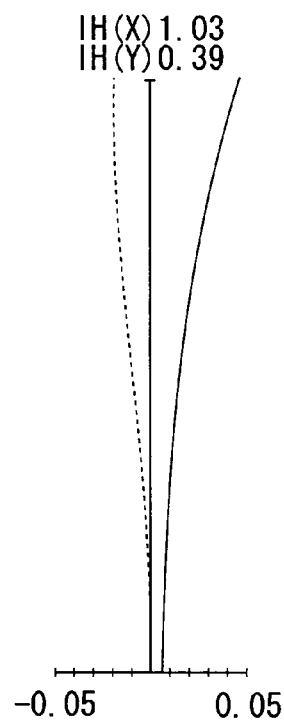
FIG. 17C is an aberration diagram showing astigmatism with the lens configuration shown in FIGS. 16A and 16B, the solid line corresponding to the sagittal direction (YZ direction), and the broken line corresponding to the meridional direction (XZ direction).
Figure 17D:
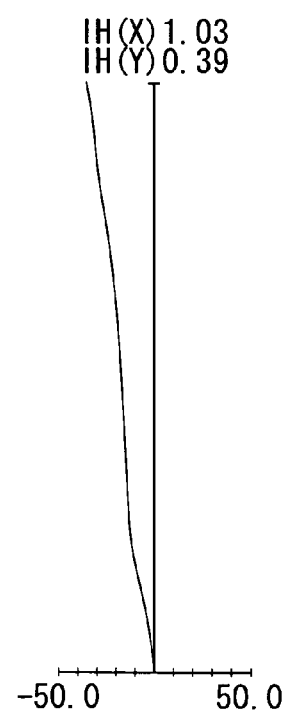
FIG. 17D is a distortion diagram in the diagonal direction of the lens configuration shown in FIGS. 16A and 16B.
Figure 17E:
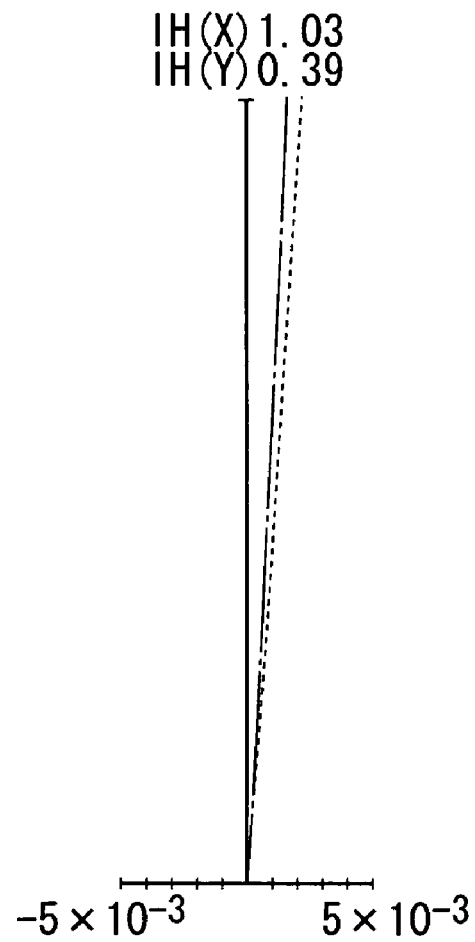
FIG. 17E is a magnification chromatic aberration diagram in the diagonal direction of the lens configuration shown in FIGS. 16A and 16B.

FIG. 17A is a spherical aberration diagram in the XZ cross-section, FIG. 17B is a spherical aberration diagram in the YZ cross-section, and FIG. 17C is a diagram of astigmatism, in which the solid line represents aberration in the sagittal direction (YZ direction), and the broken line represents aberration in the meridional direction (XZ direction), FIG. 17D is a distortion diagram in the diagonal direction, and FIG. 17E is a magnification chromatic aberration diagram in the diagonal direction. Furthermore, in FIGS. 17A and 17E, the solid line represents aberration at the e-line (546.07 nm), the one-dot chain line represents aberration at the F-line (486.13 nm), and the broken line represents aberration at the C-line (656.27 nm).

Surface Data

| surface number | r | d | ne | vd |
| --- | --- | --- | --- | --- |
| object plane | ∞ | 26.5 | | |
| 1 | 29.051 | 0.443 | 1.88815 | 40.76 |
| 2 | 3.744 | 0.296 | | |
| 3$ | 5.792 | 0.24 | 2.01169 | 28.27 |
| 4$ | 2.457 | 0.377 | | |
| 5 | ∞ | 6.2 | 2.01169 | 28.27 |
| 6 | ∞ | 0.01 | | |
| 7$ | 3.173 | 0.332 | 1.77621 | 49.6 |
| 8$ | 9.972 | 0.217 | | |
| 9 (stop) | ∞ | 0.106 | | |
| 10 | −421.796 | 0.286 | 1.93429 | 18.9 |
| 11 | −9.291 | 0.425 | | |
| 12 | ∞ | 0.343 | 1.51825 | 64.14 |
| 13 | ∞ | 0.425 | | |
| 14 | 129.676 | 1.68 | 1.48915 | 70.23 |
| 15 | −1.471 | 0.381 | 1.85504 | 23.78 |
| 16 | −5.445 | 0.135 | | |
| 17 | 32.806 | 0.742 | 1.77621 | 49.6 |
| 18 | −4.321 | 0.165 | | |
| 19 | ∞ | 4.2 | 1.51825 | 64.14 |
| 20 | ∞ | 0.369 | | |
| 21 | ∞ | 0.9 | 1.51825 | 64.14 |
| 22 | ∞ | 0.7 | 1.50801 | 60 |
| image plane | ∞ | 0 | | |

Aspherical Surface Data

| | RDX | RDY |
| --- | --- | --- |
| third surface TOC | 5.792 | −4.226 |
| fourth surface TOC | 2.457 | 1.899 |
| seventh surface TOC | 3.173 | 3.495 |
| eighth surface TOC | 9.972 | 92.384 |

The stereoscopic image-capturing objective optical system according to Examples 1 to 5 above satisfies the following Conditional Expressions (1) to (9).

$0.4 \leq$ vertical focal length/horizontal focal length $\leq 0.7$     Conditional Expression (1)

$-3 \leq$ first lens/horizontal focal length $\leq -1.5$     Conditional Expression (2)

$2 \leq 2\text{-}O$ vertical/horizontal focal length $\leq 7.5$     Conditional Expression (3)

$2.1 \leq 5\text{-}TO$/horizontal focal length $\leq 6.6$     Conditional Expression (4)

$0.8 \leq$ second anamorphic surface $R$ ratio(horizontal/vertical) $\leq 2.75$     Conditional Expression (5)

$0 \leq$ fourth anamorphic surface $R$ ratio(horizontal/vertical) $\leq 1.6$     Conditional Expression (6)

$0.45 \leq$ first reflecting surface distance/horizontal focal length $\leq 2.2$     Conditional Expression (7)

$0.7 \leq$ second reflecting surface distance/vertical focal length $\leq 4.5$     Conditional Expression (8)

$1.2 \leq$ combined focal length behind stop/horizontal focal length $\leq 2.8$     Conditional Expression (9)

Conditional Expression (1) is a conditional expression corresponding to the vertical and horizontal dimensions of the image-capturing surface. If the range of Conditional Expression (1) is exceeded, an unnatural image will result because the significance of the distortion differs between the vertical and horizontal directions.

Conditional Expression (2) is a conditional expression for correcting center astigmatism. The greater the power, the greater the center astigmatism, and the smaller the power, the greater the beam height at the first lens, leading to an increase in the size of the system. In addition, the pantoscopic lenses interfere with each other, making layout difficult.

Conditional Expression (3) is a conditional expression necessary for correcting vertical and horizontal coma and for matching the image plane positions by respectively controlling the vertical and horizontal coma, because the amount of field curvature in the vertical direction does not always agree with that in the horizontal direction. If the range of Conditional Expression (3) is exceeded, a change in the amount of field curvature cannot be compensated for by correction of coma, and thus, the vertical and horizontal image plane positions are not aligned.

Conditional Expression (4) corresponds to the power arrangement of a cemented lens and corrects axial chromatic aberration and magnification chromatic aberration. The smaller the power, the greater the magnification chromatic aberration, and the greater the power, the smaller the magnification chromatic aberration, which, however, makes correction of axial chromatic aberration difficult.

Conditional Expressions (5) and (6) are conditional expressions for correcting astigmatism, which represent the ranges of the R ratios of the anamorphic surfaces. If the ranges of Conditional Expressions (5) and (6) are exceeded, not only center astigmatism, but also significant peripheral astigmatism occurs. If the upper limits of Conditional Expressions (5) and (6) are exceeded, the sagittal image plane tends to be over in the horizontal direction, and the meridional image plane tends to be under. If the lower limits of Conditional Expressions (5) and (6) are exceeded, the sagittal image plane tends to be under, and the meridional image plane tends to be over in the same horizontal direction.

Conditional Expressions (7) and (8) are conditional expressions for introducing reflecting surfaces. At the lower limits of Conditional Expressions (7) and (8), a space big enough to introduce the reflecting surfaces, necessary in the layout, cannot be ensured. However, if the upper limits are exceeded, a space that is larger than required is used, making the overall length of the optical system too large, which is not preferable from the standpoint of the layout.

Conditional Expression (9) is a conditional expression for reducing the size of the entire system. If the upper limit of Conditional Expression (9) is exceeded and the power of the positive group behind the stop is small, the overall length increases, which is not preferable. If the lower limit of Conditional Expression (9) is exceeded and the power is large, the back focal length is short, making it difficult to ensure a space for providing the reflective member.

{Reference Signs List}

| | |
|---|---|
| 1: | stereoscopic image-capturing objective optical system |
| 2: | first lens group (a pair of negative lens groups) |
| 3: | prism (first prisms) |
| 3c, 5c: | reflecting surface |
| 4: | second lens group (a pair of positive lens groups) |
| 5: | prism (second prisms) |
| 5b: | exit surface |
| 6a: | image-capturing surface |

The invention claimed is:

1. A stereoscopic image-capturing objective optical system comprising:
a first prism pair that converts beams emitted from a single subject and having two substantially parallel optical axes arranged side-by-side in one direction with a certain distance therebetween into beams arranged side-by-side in a direction intersecting the aforementioned side-by-side direction with a certain distance therebetween; and
a second prism pair that performs conversion to reduce the distance between the optical axes of the two beams converted by the first prism pair and that has exit surfaces arranged side-by-side in a direction perpendicular to the side-by-side arrangement direction before entering the first prism pair, wherein
the first prism pair includes a first parallelogram prism that reflects, only twice, the beam containing one of the two optical axes in a first plane containing said one of the optical axes, and
a second parallelogram prism that reflects, only twice, the beam containing the other of the two optical axes in a second plane containing the other optical axis and parallel to the first plane with a certain distance therebetween, and
wherein the first and second parallelogram prisms convert the beams having two substantially parallel optical axes arranged side-by-side in one direction with the certain distance therebetween into the beams arranged side-by-side in the direction intersecting the aforementioned side-by-side arrangement direction with the certain distance therebetween.

2. The stereoscopic image-capturing objective optical system according to claim 1, wherein the first prism pair converts the two beams such that the beams are arranged in a direction perpendicular to the side-by-side direction.

3. The stereoscopic image-capturing objective optical system according to claim 1, wherein
each prism constituting the first prism pair shifts the beam incident thereon in a direction perpendicular to the side-by-side direction, and
each prism constituting the second prism pair shifts the beam incident thereon in a direction parallel to the side-by-side direction.

4. The stereoscopic image-capturing objective optical system according to claim 1, comprising, in sequence from an object side, a pair of negative lens groups, the first prism pair, a pair of positive lens groups, and the second prism pair,
wherein two substantially parallel beams that exit from the second prism pair are allowed to be incident on an image-capturing surface.

5. The stereoscopic image-capturing objective optical system according to claim 4,
wherein one or more of the lenses constituting the lens groups has a toric surface that gives the beams incident on the image-capturing surface a smaller magnification in the direction perpendicular to the side-by-side direction than in the side-by-side direction before entering the first prism pair.

6. The stereoscopic image-capturing objective optical system according to claim 5, further comprising a stop that narrows the beams,
wherein the toric surface is disposed on the object side with respect to the stop.

7. An endoscope comprising a stereoscopic image-capturing objective optical system according to claim 1 at the tip of an insertion portion thereof.

* * * * *